(12) United States Patent
Lu et al.

(10) Patent No.: US 7,645,859 B2
(45) Date of Patent: Jan. 12, 2010

(54) TUMOUR SUPPRESSOR PROTEIN

(75) Inventors: Xin Lu, London (GB); Elizabeth Slee, London (GB)

(73) Assignee: Ludwig Institute For Cancer Research, Zurich (CH)

( * ) Notice: Subject to any disclaimer, the term of this patent is extended or adjusted under 35 U.S.C. 154(b) by 70 days.

(21) Appl. No.: 10/582,316

(22) PCT Filed: Aug. 13, 2004

(86) PCT No.: PCT/GB2004/003492

§ 371 (c)(1), (2), (4) Date: Feb. 20, 2007

(87) PCT Pub. No.: WO2005/056592

PCT Pub. Date: Jun. 23, 2005

(65) Prior Publication Data

US 2007/0128157 A1    Jun. 7, 2007

Related U.S. Application Data

(60) Provisional application No. 60/554,990, filed on Mar. 19, 2004.

(30) Foreign Application Priority Data

Dec. 10, 2003   (GB) ................................ 0328690.3

(51) Int. Cl.
*C07K 14/00* (2006.01)
(52) U.S. Cl. ...................................... 530/350; 530/828
(58) Field of Classification Search ................. 530/350, 530/828
See application file for complete search history.

(56) References Cited

FOREIGN PATENT DOCUMENTS

| WO | WO 02/12325 A2 | 2/2002 |
|---|---|---|
| WO | WO 03/000843 A2 | 1/2003 |

OTHER PUBLICATIONS

MPSRCH search result, 2008, us-10-582-316.1.rag, result 7, pp. 1-2.*
Bork (Genome Research, 2000,10:398-400).*
Scott et al (Nature Genetics, 1999, 21:440-443).*
Bowie (Science, 1990, 257:1306-1310).*
Burgess et al ( J of Cell Bio. 111:2129-2138, 1990).*
Lazar et al (Molecular and Cellular Biology, 1988, 8:1247-1252).*
Mellman I, 2006, The Scientist, 20(1): 47-56.*
White et al, 2001 (Ann Rev Med, 52: 125-145).*
Bodey et al, 2000, Anticancer Res, 20: 2665-2676.*
Database EMBL 'Online! Accession No. BC032298 (2002).
Bergamaschi et al., "iASPP Oncoprotein is a Key Inhibitor of p53 Conserved from Worm to Human," *Nature Genetics* 33:162-167 (2003).
Yang et al., "Identification of a Novel Inhibitor of Nuclear Factor-κB, Rel A-Associated Inhibitor," *J. Biol. Chem.* 274:15662-15670 (1999).

* cited by examiner

*Primary Examiner*—Larry R. Helms
*Assistant Examiner*—Minh-Tam Davis
(74) *Attorney, Agent, or Firm*—Marshall, Gerstein & Borun LLP

(57) ABSTRACT

We describe a polypeptide which binds and modulates the activity of a tumour suppressor polypeptide, for example p53; a nucleic acid molecule encoding said protein and screening methods which modulate the binding activity of said polypeptide for its target polypeptide(s).

5 Claims, 16 Drawing Sheets

Figure 1a

MDSEAFQSARDFLDMNFQSLAMKHMDLKQMELDTAAAKVDELTKQLESLWSDSPAPPGPQAGP
PSRPPRYSSSSIPEPFGSRGSPRKAATDGADTPFGRSESAPTLHPYSPLSPKGRPSSPRTPLYLQPDAY
GSLDRATSPRPRAFDGAGSSLGRAPSPRPGPGPLRQQGPPTPFDFLGRAGSPRGSPLAEGPQAFFPE
RGPSPRPPATAYDAPASAFGSSLLGSGGSAFAPPLRAQDDLTLRRRPPKAWNESDLDVAYEKKPSQ
TASYERLDVFARPASPSLQLLPWRESSLDGLGGTGKDNLTSATLPRNYKVSPLASDRRSDAGSYRR
SLGSAGPSGTLPRSWQPVSRIPMPPSSPQPRGAPRQRPIPLSMIFKLQNAFWEHGASRAMLPGSPLF
TRAPPPKLQPQPQPQPQPQSQPQPQLPPQPQTQPQTPTPAPQHPQQTWPPVNEGPPKPPTELEPEPEI
EGLLTPVLEAGDVDEGPVARPLSPTRLQPALPPEAQSVPELEEVARVLAEIPRPLKRRGSMEQAPA
VALPPTHKKQYQQIISRLFHRHGGPGPGGPEPELSPITEGSEARAGPPAPAPPAPIPPPAPSQSSPPEQ
PQSMEMRSVLRKAGSPRKARRARLNPLVLLLDAALTGELEVVQQAVKEMNDPSQPNEEGITALH
NAICGANYSIVDFLITAGANVNSPDSHGWTPLHCAASCNDTVICMALVQHGAAIFATTLSDGATAF
EKCDPYREGYADCATYLADVEQSMGLMNSGAVYALWDYSAEFGDELSFREGESVTVLRRDGPEE
TDWWWAALHGQEGYVPRNYFGLFPRVKPQRSKV*

Figure 1b

CCACGCGTCCGGGAAGCCCCCAGGTGCCAGGATCTGCCCGGATCCGCGCCCGCTCCGGCCGG
CACCATGGACAGCGAGGCATTCCAGAGCGCGCGGGACTTTCTGGACATGAACTTCCAGTCGCT
GGCCATGAAACACATGGATCTGAAGCAGATGGAGCTGGACACGGCGGCGGCCAAGGTGGATG
AACTGACCAAGCAGCTGGAGTCGCTGTGGTCAGACTCTCCCGCGCCTCCTGGCCCGCAGGCCG
GACCCCCTTCTAGGCCGCCCCGGTACAGCTCCAGCTCGATCCCTGAGCCCTTCGGCAGCCGAG
GGTCCCCCCGGAAGGCGGCCACCGACGGCGCAGACACCCCGTTCGGACGATCAGAGAGTGCC
CCAACCCTACACCCCTACAGCCCGCTGTCCCCCAAGGGACGGCCGTCGTCGCCGCGCACCCCG
CTCTACCTGCAGCCGGACGCCTACGGCAGCCTGGACCGCGCGACCTCGCCCCGGCCCCGCGCC
TTCGATGGCGCAGGCAGCTCCCTCGGCCGTGCGCCCTCCCCGCGGCCCGGGCCAGGCCCGCTC
CGCCAGCAGGGTCCCCCCACGCCTTTCGACTTCCTGGGCCGCGCAGGCTCCCCCCGCGGCAGC
CCCCTGGCGGAGGGGCCCCAGGCCTTCTTCCCCGAGCGTGGGCCGTCACCGCGCCCCCTGCC
ACAGCCTACGACGCGCCAGCGTCCGCCTTCGGGAGCTCCCTGCTAGGCTCCGGCGGCAGCGCA
TTCGCCCCGCCTCTGCGCGCGCAAGACGACCTGACGCTGCGCCGGCGGCCTCCGAAAGCCTGG
AACGAGTCTGACCTGGACGTGGCGTACGAGAAGAAGCCTTCGCAGACAGCGAGCTATGAACG
CCTGGACGTCTTCGCAAGGCCTGCCTCGCCGAGCCTGCAGCTGTTGCCTTGGAGGGAGAGCAG
CCTGGATGGACTGGGGGGCACCGGCAAGGACAACCTCACTAGCGCCACCCTGCCGCGCAATT
ACAAGGTCTCTCCTCTGGCCAGCGACCGGCGTTCAGACGCGGGCAGCTACCGGCGCTCGCTGG
GCTCCGCGGGGCCGTCGGGCACTTTGCCTCGCAGCTGGCAGCCCGTCAGCCGCATCCCCATGC
CCCCCTCCAGCCCCCAGCCCCGCGGGCCCCGCGCCAGCGTCCCATCCCCCTCAGCATGATCT
TCAAGCTGCAGAACGCCTTCTGGGAGCACGGGGCCAGCCGCGCCATGCTCCCTGGGTCCCCCC
TCTTCACCCGAGCACCCCCGCCTAAGCTGCAGCCCCAACCACAACCACAGCCCCAGCCACAAT
CACAACCACAGCCCCAGCTGCCCCCACAGCCCCAGACCCAACCCCAAACCCCTACCCCAGCCC
CCCAGCATCCCCAACAGACATGGCCCCCTGTGAACGAAGGACCCCCCAAACCCCCCACCGAG
CTGGAGCCTGAGCCGGAGATAGAGGGGCTGCTGACACCAGTGCTGGAGGCTGGCGATGTGGA
TGAAGGCCCTGTAGCAAGGCCTCTCAGCCCCACGAGGCTGCAGCCAGCACTGCCACCGGAGG
CACAGTCGGTGCCCGAGCTGGAGGAGGTGGCACGGGTGTTGGCGGAAATTCCCCGGCCCCTC
AAACGCAGGGGCTCCATGGAGCAGGCCCCTGCTGTGGCCCTGCCCCCTACCCACAAGAAACA
GTACCAGCAGATCATCAGCCGCCTCTTCCATCGTCATGGGGGCCAGGGCCCGGGGGCCGG
AGCCAGAGCTGTCCCCCATCACTGAGGGATCTGAGGCCAGGGCAGGGCCCCCTGCTCCTGCCC
CACCAGCTCCCATTCCACCCCGGCCCCGTCCCAGAGCAGCCCACCAGAGCAGCCGCAGAGC
ATGGAGATGCGCTCTGTGCTGCGGAAGGCGGGCTCCCCGCGCAAGGCCCGCCGCGCGCCT
CAACCCTCTGGTGCTCCTCCTGGACGCGGCGCTGACCGGGGAGCTGGAGGTGGTGCAGCAGG
CGGTGAAGGAGATGAACGACCCGAGCCAGCCCAACGAGGAGGGCATCACTGCCTTGCACAAC
GCCATCTGCGGCGCCAACTACTCTATCGTGGATTTCCTCATCACCGCGGGTGCCAATGTCAAC
TCCCCCGACAGCCACGGCTGGACACCCTTGCACTGCGCGGCGTCGTGCAACGACACAGTCATC
TGCATGGCGCTGGTGCAGCACGGCGCTGCAATCTTCGCCACCACGCTCAGCGACGGCGCCACC
GCCTTCGAGAAGTGCGACCCTTACCGCGAGGGTTATGCTGACTGCGCCACCTACCTGGCAGAC
GTCGAGCAGAGTATGGGGCTGATGAACAGCGGGGCAGTGTACGCTCTCTGGGACTACAGCGC

Figure 1b continued

```
CGAGTTCGGGGACGAGCTGTCCTTCCGCGAGGGCGAGTCGGTCACCGTGCTGCGGAGGGACG
GGCCGGAGGAGACCGACTGGTGGTGGGCCGCGCTGCACGGCCAGGAGGGCTACGTGCCGCGG
AACTACTTCGGGCTGTTCCCCAGGGTGAAGCCTCAAAGGAGTAAAGTCTAGCAGGATAGAAG
GAGGTTTCTGAGGCTGACAGAAACAAGCATTCCTGCCTTCCCTCCAGACCTCTCCCTCTGTTTT
TTGCTGCCTTTATCTGCACCCCTCACCCTGCTGGTGGTGGTCCTTGCCACCGGTTCTCTGTTCTC
CTGGAAGTCCAGGGAAGAAGGAGGGCCCCAGCCTTAAATTTAGTAATCTGCCTTAGCCTTGGG
AGGTCTGGGAAGGGCTGGAAATCACTGGGGACAGGAAACCACTTCCTTTTGCCAAATCAGAT
CCCGTCCAAAGTGCCTCCCATGCCTACCACCATCATCACATCCCCCAGCAAGCCAGCCACCTG
CCCAGCCGGGCCTGGGATGGGCCACCACACCACTGGATATTCCTGGGAGTCACTGCTGACACC
ATCTCTCCCAGCAGTCTTGGGGTCTGGGTGGGAAACATTGGTCTCTACCAGGATCCCTGCCCC
ACCTCTCCCCAATTAAGTGCCTTCACACAGCTCTGGTTTAATGTTTATAAACAAAATAGAGAA
ACTTTCCTTATAAATAAAAGTAGTTTGCACAGAAAAAAAAAAAAAAA
```

Figure 2a

MWMKDPVARPLSPTRLQPALPPEAQSVPELEEVARVLAEIPRPLKRRGSMEQAPAVA
LPPTHKKQYQQIISRLFHRHGGPGPGGRSQSCPPSLRDLRPGQGPLLLPHQLPFHRPAP
SQSSPPEQPQSMEMRSVLRKAGSPRKARRARLNPLVLLLDAALTGELEVVQQAVKE
MNDPSQPNEEGITALHNAICGANYSIVDFLITAGANVNSPDSHGWTPLHCAASCNDT
VICMALVQHGAAIFATTLSDGATAFEKCDPYREGYADCATYLADVEQSMGLMNSGA
VYALWDYSAEFGDELSFREGESVTVLRRDGPEETDWWWAALHGQEGYVPRNYFGL
FPRVKPQRSKV

Figure 2b
GCGGCCGCGTCGACCCGGCGTTCAGACGCGGGCAGCTACCGGCGCTCGCTGGGTCCGCGGGGCCGTC
GGGCACTTTGCCTCGCAGCTGGCAGCCCGTCAGCCGCATCCCATGCCCCCCTCCAGCCCCAGCCCC
GCGGGGCCCCGCGCCAGCGTCCCATCCCCCTCAGCATGATCTTCAAGCTGCAGAACGCCTTCTGGGA
GCACGGGGCCAGCCGCG CCATGCTCCCTGGGTCCCCCCTCTTCACCCGAGCACCCCCGCCTAAGCTG
CAGCCCCAACCACAACCACAGCCCCAGCCACAATCACAACCACAGCCCCAGCTGCCCCAACAGCCCC
AGACCCAACCCCAAACCCCTACCCCAGCCTCCCACATCCGCATCCCCAACAGACATGGCCCCCTGTG
AACGAAGGACCCCCCAAACCCCCCACCGAGCTGGAGCCTGAGCCGGAGATAGAGGGGCTGCTGACA
CCAGTGCTGGAGGCTGGCGATGTGGATGAAGGACCCTGTAGCAAGGCCTCTCAGCCCCACGAGGCTG
CAGCCAGCACTGCCACCGGAGGCACAGTCGGTGCCCGAGCTGGAGGAGGTGGCACGGGTGTTGGCG
GAAATTCCCCGGCCCCTCAAACGCAGGGGCTCCATGGAGCAGGCCCCTGCTGTGGCCCTGCCCCCTA
CCCACAAGAAACAGTACCAGCAGATCATCAGCCGCCTCTTCCATCGTCATGGGGGGCCAGGGCCCGG
GGGGCGGAGCCAGAGCTGTCCCCCATCACTGAGGGATCTGAGGCCAGGGCAGGGCCCCCTGCTCCTG
CCCCAC CAGCTCCCATTCCACCGCCCGGCCCCGTCCCAGAGCAGCCCACCAGAGCAGCCGCAGAGC
ATGGAGATGCGCTCTGTGCTGCGGAAGGCGGGCTCCCCGCGCAAGGCCCGCCGCGCGCCTCAACC
CTCTGGTGCTCCTCCTGGACGCGGCGCTGACCGGGGAGCTGGAGGTGGTGCAGCAGGCGGTGAAGG
AGATGAACGACCCGAGCCAGCCCAACGAGGAGGGCATCACTGCCTTGCACAACGCCATCTGCGGCG
CCAACTACTCTATCGTGGATTTCCTCATCACCGCGGGTGCCAATGTCAACTCCCCCGACAGCCACGGC
TGGACACCCTTGCACTGCGCGGCGTCGTGCAACGACACAGTCATCTGCATGGCGCTGGTGCAGCACG
GCGCTG CAATCTTCGC CACCACGCTC AGCGACGGCG CCACCGCCTTCGAGAAGTGCGACCCTTACC
GCGAGGGTTATGCTGACTGCGCCACCTACCTGGCAGACGTCGAGCAGAGTATGGGGCTGATGAACA
GCGGGGCAGTGTACGCTCTCTGGGACTACAGCGCCGAGTTCGGGGACGAGCTGTCCTTCCGCGAGGG
CGAGTCGGTCACCGTGCTGCGGAGGGACGGGCCGGAGGAGACCGACTGGTGGTGGGCCGCGCTGCA
CGGCCAGGAGGGCTACGTGCCGCGGAACTACTTCGGGCTGTTCCCCAGGGTGAAGCCTCAAAGGAGT
AAAGTCTAGCAGGATAGAAGGAGGTTTCTGAGGCTGACAGAAACAAGCATTCCTGCCTTCCCTCCAG
ACCTCTC CCTCTGTTTTTTGCTGCCTT TATCTGCACC CCTCACCCTG CTGGTGGTGG TCCTTGCCAC
CGGTTCTCTGTTCTCCTGGAAGTCCAGGGAAGAAGGAGGGCCCCAGCCTTAAATTTAGTAATCTGCC
TTAGCCTTGGGAGGTCTGGGAAGGGCTGGAAATCACTGGGGACAGGAAACCACTTCCTTTTGCCAAA
TCAGAT CCCGTCCAAA GTGCCTCCCA TGCCTACCAC CATCATCACA TCCCCCAGCAAGCCAGCCAC
CTGCCCAGCCGGGCCTGGGATGGGCCACCACACCACTGGATATTCCTGGGAGTCACTGCTGACACCA
TCTCTCCCAGCAGTCTTGGGGTCTGGGTGGGAAACATTGGTCTCTACCAGGATCCCTGCCCCACCTCT
CCCCA ATTAAGTGCC TTCACACAGC ACTGGTTTAATGTTTATAAA CAAAATAGAG AAACTGGTTT
AATGTTTATA AACAAAATAG AGAAACTTTCGCTTATAAAT AAAAGTAGTT TGCACAGAAA
TGAAAAAAAA AAAAAAAAAA AAAAAA

Figure 3.1

| | 10 | 20 | 30 | 40 | 50 | 60 | 70 | iASPP
RAI
RAI 2.6 kb corr. translation

| | 80 | 90 | 100 | 110 | 120 | 130 | 140 | iASPP
RAI
RAI 2.6 kb corr. translation

| | 150 | 160 | 170 | 180 | 190 | 200 | 210 | iASPP
RAI
RAI 2.6 kb corr. translation

| | 220 | 230 | 240 | 250 | 260 | 270 | 280 | iASPP
RAI
RAI 2.6 kb corr. translation

| | 290 | 300 | 310 | 320 | 330 | 340 | 350 | iASPP
RAI
RAI 2.6 kb corr. translation

| | 360 | 370 | 380 | 390 | 400 | 410 | 420 | iASPP
RAI
RAI 2.6 kb corr. translation

| | 430 | 440 | 450 | 460 | 470 | 480 | 490 | iASPP      P Q P Q T Q P Q   P T P     Q H P Q Q T W P P V N E
RAI
RAI 2.6 kb corr. translation   M P W K L W R G   V G C     G D L S S D G L L F R L                           M W M K D

| | 500 | 510 | 520 | 530 | 540 | 550 | 560 | iASPP
RAI
RAI 2.6 kb corr. translation

Peptide antigen (pAbiASPP18)

| | 570 | 580 | 590 | 600 | 610 | 620 | 630 | iASPP
RAI            R S Q S C P   S L R D L R P G Q     L   L P H Q     P H R
RAI 2.6 kb corr. translation Fragment used to generate LX049.3 (not frameshift)

| | 640 | 650 | 660 | 670 | 680 | 690 | 700 | iASPP
RAI
RAI 2.6 kb corr. translation

| | 710 | 720 | 730 | 740 | 750 | 760 | 770 | iASPP
RAI
RAI 2.6 kb corr. translation

| | 780 | 790 | 800 | 810 | 820 | 830 | 840 | iASPP
RAI
RAI 2.6 kb corr. translation

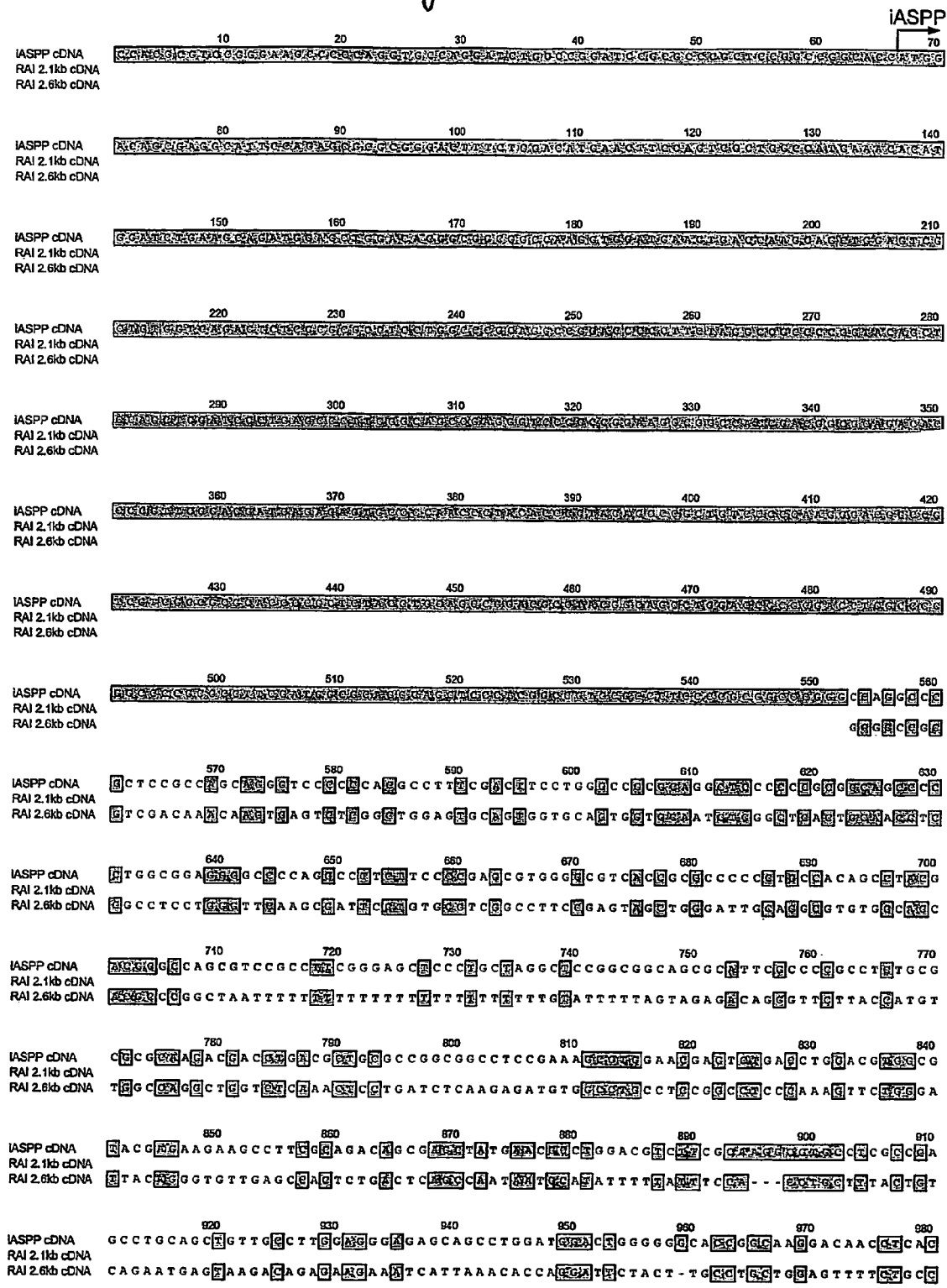
Figure 3.2

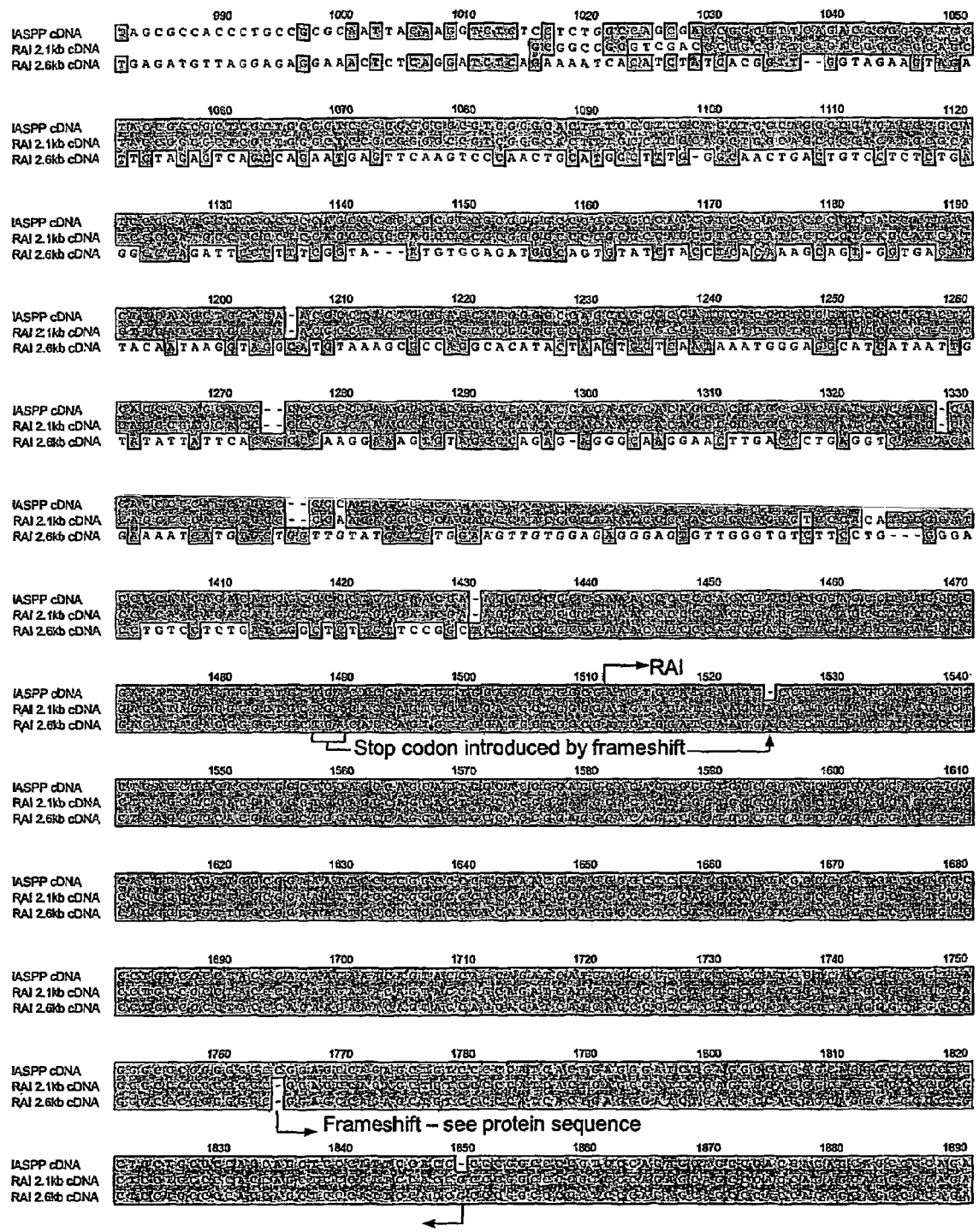
Figure 3.3

Figure 3.4

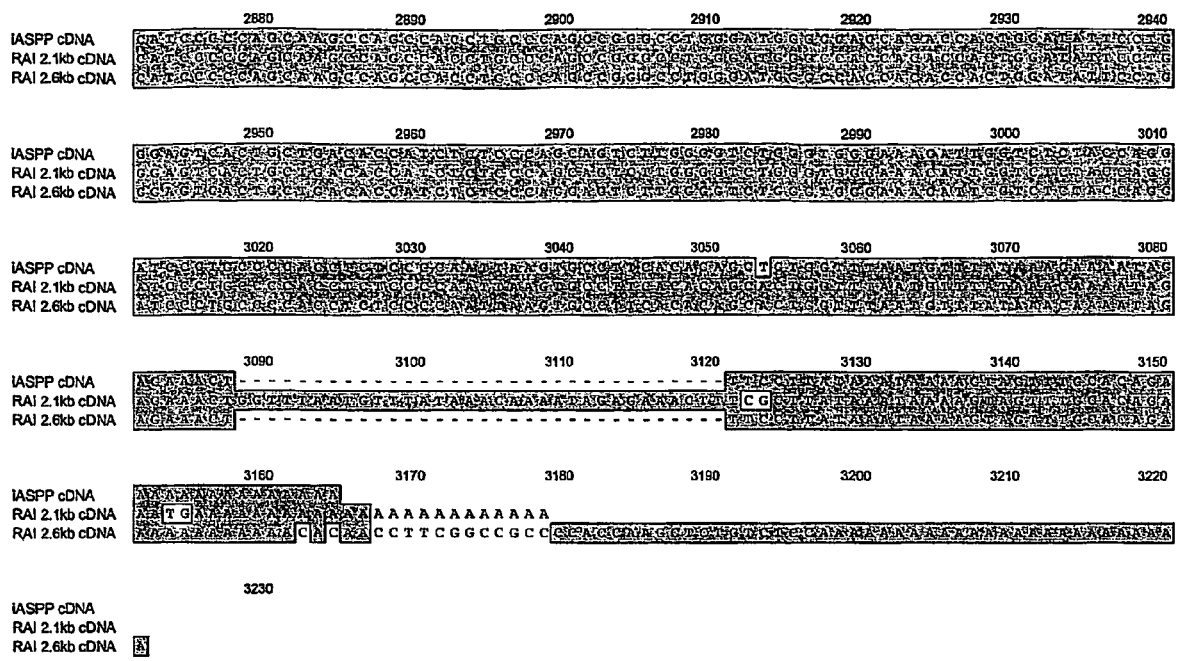
Figure 3.5

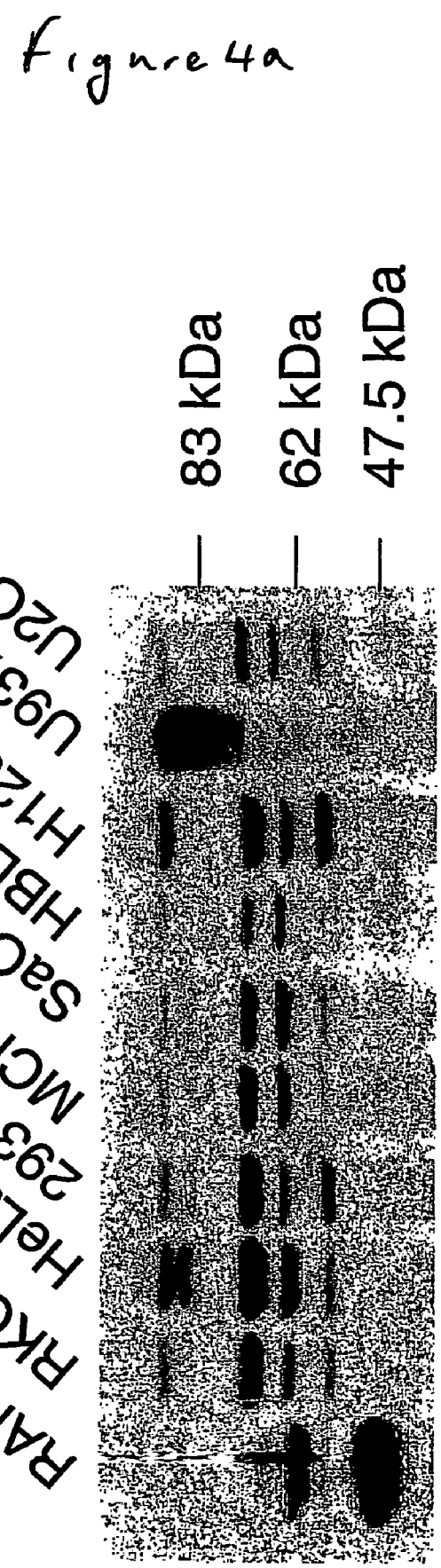

Effect of cell density and MG132 upon iASPP expression in U2OS cells

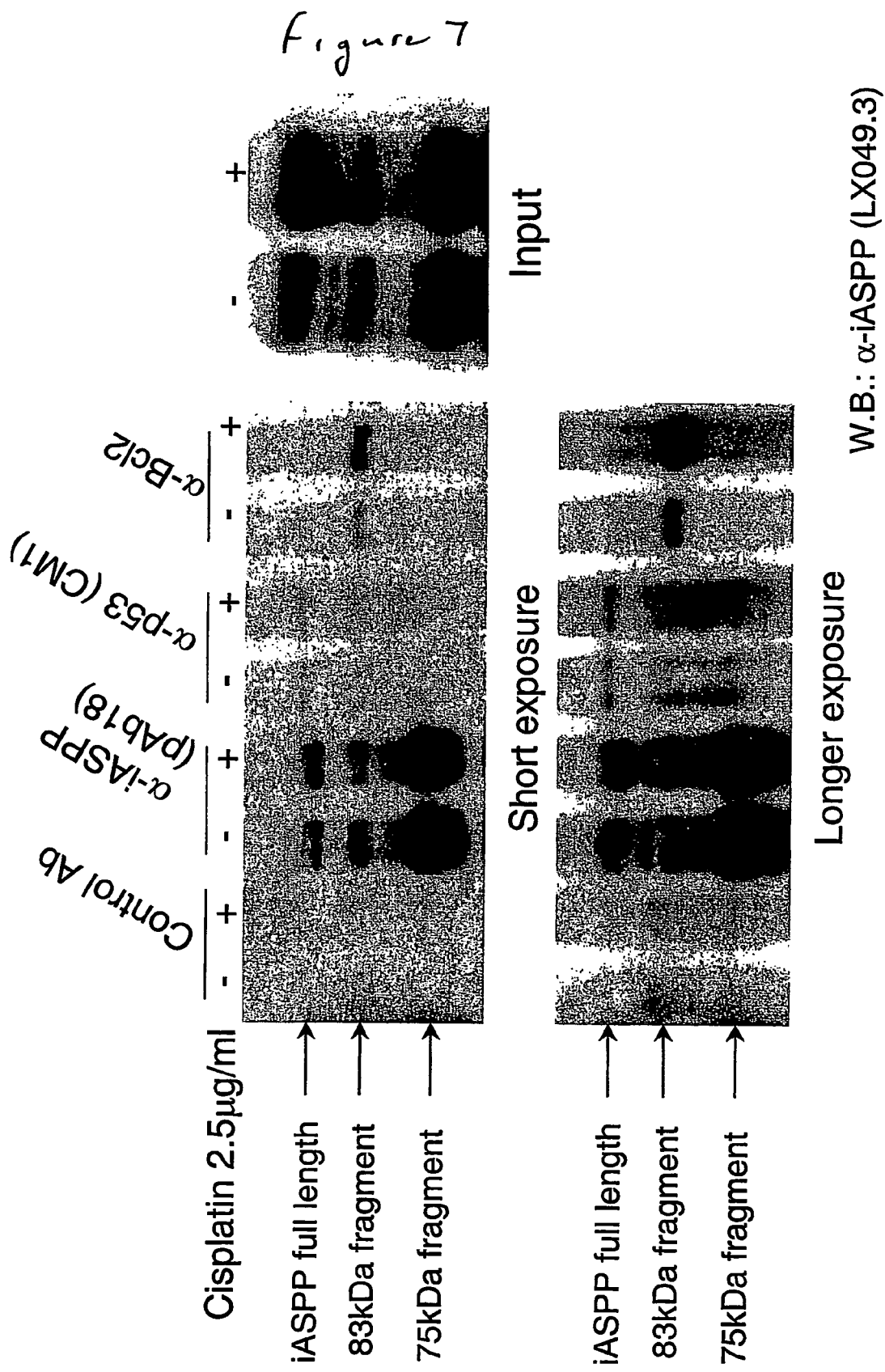

SEQUENCE LISTING

```
<160> NUMBER OF SEQ ID NOS: 7

<210> SEQ ID NO 1
<211> LENGTH: 828
```

```
<212> TYPE: PRT
<213> ORGANISM: Homo sapiens

<400> SEQUENCE: 1

Met Asp Ser Glu Ala Phe Gln Ser Ala Arg Asp Phe Leu Asp Met Asn
1               5                   10                  15

Phe Gln Ser Leu Ala Met Lys His Met Asp Leu Lys Gln Met Glu Leu
            20                  25                  30

Asp Thr Ala Ala Ala Lys Val Asp Glu Leu Thr Lys Gln Leu Glu Ser
        35                  40                  45

Leu Trp Ser Asp Ser Pro Ala Pro Pro Gly Pro Gln Ala Gly Pro Pro
    50                  55                  60

Ser Arg Pro Pro Arg Tyr Ser Ser Ser Ile Pro Glu Pro Phe Gly
65                  70                  75                  80

Ser Arg Gly Ser Pro Arg Lys Ala Ala Thr Asp Gly Ala Asp Thr Pro
                85                  90                  95

Phe Gly Arg Ser Glu Ser Ala Pro Thr Leu His Pro Tyr Ser Pro Leu
                100                 105                 110

Ser Pro Lys Gly Arg Pro Ser Ser Pro Arg Thr Pro Leu Tyr Leu Gln
            115                 120                 125

Pro Asp Ala Tyr Gly Ser Leu Asp Arg Ala Thr Ser Pro Arg Pro Arg
    130                 135                 140

Ala Phe Asp Gly Ala Gly Ser Ser Leu Gly Arg Ala Pro Ser Pro Arg
145                 150                 155                 160

Pro Gly Pro Gly Pro Leu Arg Gln Gln Gly Pro Pro Thr Pro Phe Asp
                165                 170                 175

Phe Leu Gly Arg Ala Gly Ser Pro Arg Gly Ser Pro Leu Ala Glu Gly
                180                 185                 190

Pro Gln Ala Phe Phe Pro Glu Arg Gly Pro Ser Pro Arg Pro Pro Ala
            195                 200                 205

Thr Ala Tyr Asp Ala Pro Ala Ser Ala Phe Gly Ser Ser Leu Leu Gly
    210                 215                 220

Ser Gly Gly Ser Ala Phe Ala Pro Pro Leu Arg Ala Gln Asp Asp Leu
225                 230                 235                 240

Thr Leu Arg Arg Arg Pro Pro Lys Ala Trp Asn Glu Ser Asp Leu Asp
                245                 250                 255

Val Ala Tyr Glu Lys Lys Pro Ser Gln Thr Ala Ser Tyr Glu Arg Leu
                260                 265                 270

Asp Val Phe Ala Arg Pro Ala Ser Pro Ser Leu Gln Leu Leu Pro Trp
            275                 280                 285

Arg Glu Ser Ser Leu Asp Gly Leu Gly Gly Thr Gly Lys Asp Asn Leu
    290                 295                 300

Thr Ser Ala Thr Leu Pro Arg Asn Tyr Lys Val Ser Pro Leu Ala Ser
305                 310                 315                 320

Asp Arg Arg Ser Asp Ala Gly Ser Tyr Arg Arg Ser Leu Gly Ser Ala
                325                 330                 335

Gly Pro Ser Gly Thr Leu Pro Arg Ser Trp Gln Pro Val Ser Arg Ile
                340                 345                 350

Pro Met Pro Pro Ser Ser Pro Gln Arg Gly Ala Pro Arg Gln Arg
            355                 360                 365

Pro Ile Pro Leu Ser Met Ile Phe Lys Leu Gln Asn Ala Phe Trp Glu
    370                 375                 380

His Gly Ala Ser Arg Ala Met Leu Pro Gly Ser Pro Leu Phe Thr Arg
385                 390                 395                 400
```

```
Ala Pro Pro Pro Lys Leu Gln Pro Gln Pro Gln Pro Gln Pro
                405                 410                 415
Gln Ser Gln Pro Gln Pro Gln Leu Pro Pro Gln Pro Gln Thr Gln Pro
            420                 425                 430
Gln Thr Pro Thr Pro Ala Pro Gln His Pro Gln Gln Thr Trp Pro Pro
            435                 440                 445
Val Asn Glu Gly Pro Pro Lys Pro Pro Thr Glu Leu Glu Pro Glu Pro
    450                 455                 460
Glu Ile Glu Gly Leu Leu Thr Pro Val Leu Glu Ala Gly Asp Val Asp
465                 470                 475                 480
Glu Gly Pro Val Ala Arg Pro Leu Ser Pro Thr Arg Leu Gln Pro Ala
                485                 490                 495
Leu Pro Pro Glu Ala Gln Ser Val Pro Glu Leu Glu Glu Val Ala Arg
            500                 505                 510
Val Leu Ala Glu Ile Pro Arg Pro Leu Lys Arg Gly Ser Met Glu
    515                 520                 525
Gln Ala Pro Ala Val Ala Leu Pro Pro Thr His Lys Lys Gln Tyr Gln
530                 535                 540
Gln Ile Ile Ser Arg Leu Phe His Arg His Gly Pro Gly Pro Gly
545                 550                 555                 560
Gly Pro Glu Pro Glu Leu Ser Pro Ile Thr Glu Gly Ser Glu Ala Arg
                565                 570                 575
Ala Gly Pro Pro Ala Pro Ala Pro Pro Ala Pro Ile Pro Pro Ala
            580                 585                 590
Pro Ser Gln Ser Ser Pro Pro Glu Gln Pro Gln Ser Met Glu Met Arg
    595                 600                 605
Ser Val Leu Arg Lys Ala Gly Ser Pro Arg Lys Ala Arg Arg Ala Arg
    610                 615                 620
Leu Asn Pro Leu Val Leu Leu Asp Ala Ala Leu Thr Gly Glu Leu
625                 630                 635                 640
Glu Val Val Gln Gln Ala Val Lys Glu Met Asn Asp Pro Ser Gln Pro
                645                 650                 655
Asn Glu Glu Gly Ile Thr Ala Leu His Asn Ala Ile Cys Gly Ala Asn
            660                 665                 670
Tyr Ser Ile Val Asp Phe Leu Ile Thr Ala Gly Ala Asn Val Asn Ser
            675                 680                 685
Pro Asp Ser His Gly Trp Thr Pro Leu His Cys Ala Ala Ser Cys Asn
    690                 695                 700
Asp Thr Val Ile Cys Met Ala Leu Val Gln His Gly Ala Ala Ile Phe
705                 710                 715                 720
Ala Thr Thr Leu Ser Asp Gly Ala Thr Ala Phe Glu Lys Cys Asp Pro
                725                 730                 735
Tyr Arg Glu Gly Tyr Ala Asp Cys Ala Thr Tyr Leu Ala Asp Val Glu
            740                 745                 750
Gln Ser Met Gly Leu Met Asn Ser Gly Ala Val Tyr Ala Leu Trp Asp
            755                 760                 765
Tyr Ser Ala Glu Phe Gly Asp Glu Leu Ser Phe Arg Glu Gly Glu Ser
    770                 775                 780
Val Thr Val Leu Arg Arg Asp Gly Pro Glu Glu Thr Asp Trp Trp Trp
785                 790                 795                 800
Ala Ala Leu His Gly Gln Glu Gly Tyr Val Pro Arg Asn Tyr Phe Gly
                805                 810                 815
```

```
Leu Phe Pro Arg Val Lys Pro Gln Arg Ser Lys Val
            820                 825

<210> SEQ ID NO 2
<211> LENGTH: 3117
<212> TYPE: DNA
<213> ORGANISM: Homo sapiens

<400> SEQUENCE: 2
ccacgcgtcc gggaagcccc caggtgccag gatctgcccg gatccgcgcc cgctccggcc      60
ggcaccatgg acagcgaggc attccagagc gcgcgggact ttctggacat gaacttccag     120
tcgctggcca tgaaacacat ggatctgaag cagatggagc tggacacggc ggcggccaag     180
gtggatgaac tgaccaagca gctggagtcg ctgtggtcag actctcccgc gcctcctggc     240
ccgcaggccg acccccttc taggccgccc cggtacagct ccagctcgat ccctgagccc     300
ttcggcagcc gagggtcccc ccggaaggcg ccaccgacg cgcagacac cccgttcgga      360 cgatcagaga gtgccccaac cctacacccc tacagcccgc tgtcccccaa gggacggccg     420
tcgtcgccgc gcaccccgct ctacctgcag ccggacgcct acggcagcct ggaccgcgcg     480
acctcgcccc ggccccgcgc cttcgatggc gcaggcagct ccctcggccg tgcgccctcc     540
ccgcggcccg ggccaggccc gctccgccag cagggtcccc ccacgccttt cgacttcctg     600
ggccgcgcag gctcccccg cggcagcccc ctggcggagg ggccccaggc cttcttcccc     660
gagcgtgggc cgtcaccgcg cccccctgcc acagcctacg acgcgccagc gtccgccttc     720
gggagctccc tgctaggctc cggcggcagc gcattcgccc cgcctctgcg cgcgcaagac     780
gacctgacgc tgcgccggcg gcctccgaaa gcctggaacg agtctgacct ggacgtggcg     840
tacgagaaga gccttcgca gacagcgagc tatgaacgcc tggacgtctt cgcaaggcct     900
gcctcgccga gctgcagct gttgccttgg agggagagca gcctggatgg actgggggc      960 accggcaagg acaacctcac tagcgccacc ctgccgcgca attacaaggt ctctcctctg    1020
gccagcgacc ggcgttcaga cgcgggcagc taccggcgct cgctgggctc cgcggggccg    1080
tcgggcactt tgcctcgcag ctggcagccc gtcagccgca tcccatgcc cctccagc      1140 ccccagcccc gcgggcccc gcgccagcgt cccatccccc tcagcatgat cttcaagctg    1200
cagaacgcct tctgggagca cggggccagc gcgccatgc tccctgggtc ccccctcttc    1260
acccgagcac ccccgcctaa gctgcagccc caaccacaac cacagcccca gccacaatca    1320
caaccacagc cccagctgcc cccacagccc cagacccaac ccaaaccccc taccccagcc    1380
ccccagcatc cccaacagac atggccccct gtgaacgaag gaccccccaa acccccacc    1440 gagctggagc tgagccgga gatagagggg ctgctgacac cagtgctgga ggctggcgat   1500
gtggatgaag gccctgtagc aaggcctctc agccccacga ggctgcagcc agcactgcca    1560
ccggaggcac agtcggtgcc cgagctggag gaggtggcac gggtgttggc ggaaattccc    1620
cggcccctca acgcagggg ctccatggag caggcccctg ctgtggccct gccccctacc    1680
cacaagaaac agtaccagca gatcatcagc cgcctcttcc atcgtcatgg ggggccaggg    1740 cccgggggc cggagccaga gctgtccccc atcactgagg gatctgaggc cagggcaggg    1800 cccccctgctc ctgccccacc agctcccatt ccacccccgg ccccgtccca gagcagccca    1860
ccagagcagc cgcagagcat ggagatgcgc tctgtgctgc ggaaggcggg ctcccgcgc    1920 aaggcccgcc gcgcgcgcct caaccctctg gtgctcctcc tggacgcggc gctgaccggg    1980
gagctggagg tggtgcagca ggcggtgaag gagatgaacg acccgagcca gcccaacgag    2040
```

```
gagggcatca ctgccttgca caacgccatc tgcggcgcca actactctat cgtggatttc    2100
ctcatcaccg cgggtgccaa tgtcaactcc cccgacagcc acggctggac acccttgcac    2160
tgcgcggcgt cgtgcaacga cacagtcatc tgcatggcgc tggtgcagca cggcgctgca    2220
atcttcgcca ccacgctcag cgacggcgcc accgccttcg agaagtgcga cccttaccgc    2280
gagggttatg ctgactgcgc cacctacctg gcagacgtcg agcagagtat ggggctgatg    2340
aacagcgggg cagtgtacgc tctctgggac tacagcgccg agttcgggga cgagctgtcc    2400
ttccgcgagg gcgagtcggt caccgtgctg cggagggacg ggccggagga gaccgactgg    2460
tggtgggccg cgctgcacgg ccaggagggc tacgtgccgc ggaactactt cgggctgttc    2520
cccagggtga agcctcaaag gagtaaagtc tagcaggata aaggaggtt tctgaggctg    2580 acagaaacaa gcattcctgc cttccctcca gacctctccc tctgtttttt gctgcctta    2640 tctgcacccc tcaccctgct ggtggtggtc cttgccaccg ttctctgtt ctcctggaag    2700 tccaggaag aaggagggcc ccagccttaa atttagtaat ctgccttagc cttgggaggt    2760
ctgggaaggg ctggaaatca ctggggacag gaaaccactt ccttttgcca aatcagatcc    2820
cgtccaaagt gcctcccatg cctaccacca tcatcacatc ccccagcaag ccagccacct    2880
gcccagccgg gcctgggatg ggccaccaca ccactggata ttcctgggag tcactgctga    2940
caccatctct cccagcagtc ttggggtctg ggtgggaaac attggtctct accaggatcc    3000 ctgcccacc tctcccaat taagtgcctt cacacagctc tggtttaatg tttataaaca    3060
aaatagagaa actttcctta taaataaaag tagtttgcac agaaaaaaaa aaaaaaa    3117
```

<210> SEQ ID NO 3
<211> LENGTH: 351
<212> TYPE: PRT
<213> ORGANISM: Homo sapiens

<400> SEQUENCE: 3

```
Met Trp Met Lys Asp Pro Val Ala Arg Pro Leu Ser Pro Thr Arg Leu
1               5                   10                  15

Gln Pro Ala Leu Pro Pro Glu Ala Gln Ser Val Pro Glu Leu Glu Glu
            20                  25                  30

Val Ala Arg Val Leu Ala Glu Ile Pro Arg Pro Leu Lys Arg Arg Gly
        35                  40                  45

Ser Met Glu Gln Ala Pro Ala Val Ala Leu Pro Pro Thr His Lys Lys
    50                  55                  60

Gln Tyr Gln Gln Ile Ile Ser Arg Leu Phe His Arg His Gly Gly Pro
65                  70                  75                  80

Gly Pro Gly Gly Arg Ser Gln Ser Cys Pro Pro Ser Leu Arg Asp Leu
                85                  90                  95

Arg Pro Gly Gln Gly Pro Leu Leu Leu Pro His Gln Leu Pro Phe His
            100                 105                 110

Arg Pro Ala Pro Ser Gln Ser Ser Pro Pro Glu Gln Pro Gln Ser Met
        115                 120                 125

Glu Met Arg Ser Val Leu Arg Lys Ala Gly Ser Pro Arg Lys Ala Arg
    130                 135                 140

Arg Ala Arg Leu Asn Pro Leu Val Leu Leu Asp Ala Ala Leu Thr
145                 150                 155                 160

Gly Glu Leu Glu Val Val Gln Gln Ala Val Lys Glu Met Asn Asp Pro
                165                 170                 175

Ser Gln Pro Asn Glu Glu Gly Ile Thr Ala Leu His Asn Ala Ile Cys
            180                 185                 190
```

```
Gly Ala Asn Tyr Ser Ile Val Asp Phe Leu Ile Thr Ala Gly Ala Asn
            195                 200                 205

Val Asn Ser Pro Asp Ser His Gly Trp Thr Pro Leu His Cys Ala Ala
        210                 215                 220

Ser Cys Asn Asp Thr Val Ile Cys Met Ala Leu Val Gln His Gly Ala
225                 230                 235                 240

Ala Ile Phe Ala Thr Thr Leu Ser Asp Gly Ala Thr Ala Phe Glu Lys
                245                 250                 255

Cys Asp Pro Tyr Arg Glu Gly Tyr Ala Asp Cys Ala Thr Tyr Leu Ala
            260                 265                 270

Asp Val Glu Gln Ser Met Gly Leu Met Asn Ser Gly Ala Val Tyr Ala
        275                 280                 285

Leu Trp Asp Tyr Ser Ala Glu Phe Gly Asp Glu Leu Ser Phe Arg Glu
    290                 295                 300

Gly Glu Ser Val Thr Val Leu Arg Arg Asp Gly Pro Glu Glu Thr Asp
305                 310                 315                 320

Trp Trp Trp Ala Ala Leu His Gly Gln Glu Gly Tyr Val Pro Arg Asn
                325                 330                 335

Tyr Phe Gly Leu Phe Pro Arg Val Lys Pro Gln Arg Ser Lys Val
            340                 345                 350

<210> SEQ ID NO 4
<211> LENGTH: 2154
<212> TYPE: DNA
<213> ORGANISM: Homo sapiens

<400> SEQUENCE: 4
gcggccgcgt cgacccggcg ttcagacgcg ggcagctacc ggcgctcgct gggtccgcgg      60
ggccgtcggg cactttgcct cgcagctggc agccgtcag ccgcatccca tgccccctc     120 cagcccccag ccccgcgggg ccccgcgcca gcgtcccatc ccctcagca tgatcttcaa     180 gctgcagaac gccttctggg agcacggggc cagccgcgcc atgctccctg gtccccct      240 cttcacccga gcaccccgc ctaagctgca gccccaacca caaccacagc ccagccaca     300 atcacaacca cagccccagc tgccccaaca gccccagacc caaccccaaa ccctacccc     360 agcctcccac atccgcatcc caacagaca tggcccctg tgaacgaagg accccccaaa     420 cccccaccg agctggagcc tgagccggag atagaggggc tgctgacacc agtgctggag     480
gctggcgatg tggatgaagg accctgtagc aaggcctctc agcccacga ggctgcagcc     540 agcactgcca ccggaggcac agtcggtgcc cgagctggag gaggtggcac gggtgttggc     600
ggaaattccc cggcccctca acgcagggg ctccatggag caggcccctg ctgtggccct     660 gcccctacc cacaagaaac agtaccagca gatcatcagc cgcctcttcc atcgtcatgg     720
ggggccaggg cccgggggc ggagccagag ctgtcccca tcactgaggg atctgaggcc     780 agggcaggc cccctgctcc tgccccacca gctcccattc caccgcccgg cccgtccca     840 gagcagccca ccagagcagc cgcagagcat ggagatgcgc tctgtgctgc ggaaggcggg     900
ctccccgcgc aaggcccgcc gcgcgcgcct caaccctctg gtgctcctcc tggacgcggc     960
gctgaccggg gagctggagg tggtgcagca ggcggtgaag gagatgaacg acccgagcca    1020 gccaacgag gagggcatca ctgccttgca caacgccatc tgcggcgcca actactctat    1080
cgtggatttc ctcatcaccg cgggtgccaa tgtcaactcc ccgacagcc acggctggac    1140 acccttgcac tgcgcggcgt cgtgcaacga cacagtcatc tgcatggcgc tggtgcagca    1200
```

```
cggcgctgca atcttcgcca ccacgctcag cgacggcgcc accgccttcg agaagtgcga   1260
cccttaccgc gagggttatg ctgactgcgc cacctacctg gcagacgtcg agcagagtat   1320
ggggctgatg aacagcgggg cagtgtacgc tctctgggac tacagcgccg agttcgggga   1380
cgagctgtcc ttccgcgagg gcgagtcggt caccgtgctg cggagggacg ggccggagga   1440
gaccgactgg tggtgggccg cgctgcacgg ccaggagggc tacgtgccgc ggaactactt   1500
cgggctgttc cccagggtga agcctcaaag gagtaaagtc tagcaggata gaaggaggtt   1560
tctgaggctg acagaaacaa gcattcctgc cttccctcca gacctctccc tctgtttttt   1620
gctgccttta tctgcacccc tcaccctgct ggtggtggtc cttgccaccg gttctctgtt   1680
ctcctggaag tccagggaag aaggagggcc ccagccttaa atttagtaat ctgccttagc   1740 cttggaggt ctgggaaggg ctggaaatca ctggggacag gaaaccactt ccttttgcca   1800
aatcagatcc cgtccaaagt gcctcccatg cctaccacca tcatcacatc ccccagcaag   1860
ccagccacct gcccagccgg gcctgggatg ggccaccaca ccactggata ttcctgggag   1920
tcactgctga caccatctct cccagcagtc ttggggtctg ggtgggaaac attggtctct   1980
accaggatcc ctgccccacc tctcccaat taagtgcctt cacacagcac tggtttaatg   2040
tttataaaca aaatagagaa actggtttaa tgtttataaa caaaatagag aaactttcgc   2100
ttataaataa aagtagtttg cacagaaatg aaaaaaaaaa aaaaaaaaaa aaaa          2154

<210> SEQ ID NO 5
<211> LENGTH: 64
<212> TYPE: DNA
<213> ORGANISM: Homo sapiens

<400> SEQUENCE: 5
gatcccctgt caactccccc gacagcttca agagagctgt cgggggagtt gacatttttg   60
gaaa                                                                 64

<210> SEQ ID NO 6
<211> LENGTH: 64
<212> TYPE: DNA
<213> ORGANISM: Homo sapiens

<400> SEQUENCE: 6
agcttttcca aaaatgtcaa ctcccccgac agctctcttg aagctgtcgg gggagttgac   60
aggg                                                                 64

<210> SEQ ID NO 7
<211> LENGTH: 18
<212> TYPE: PRT
<213> ORGANISM: Homo sapiens

<400> SEQUENCE: 7

Arg Leu Gln Pro Ala Leu Pro Pro Glu Ala Gln Ser Val Pro Glu Leu
1               5                   10                  15
Glu Glu
```

TUMOUR SUPPRESSOR PROTEIN

CROSS REFERENCE TO RELATED APPLICATIONS

This is the U.S. National Stage of International Application No. PCT/GB2004/003492, filed Aug. 13, 2004 (published in English under PCT Article 21(2)), which in turn claims the benefit of Great Britain Application No. 0328690.3, filed Dec. 10, 2003 and U.S. Provisional Application No. 60/554,990, filed Mar. 19, 2004.

FIELD

The invention relates to a protein that binds and modulates the activity of a tumour suppressor protein, for example p53; a nucleic acid molecule encoding said protein and screening methods which modulate the binding activity of said polypeptide for its target polypeptide.

BACKGROUND

Tumour suppressor genes encode proteins which function to inhibit cell growth or division and are therefore important with respect to maintaining proliferation, growth and differentiation of normal cells. Mutations in tumour suppressor genes result in abnormal cell-cycle progression whereby the normal cell-cycle check points which arrest the cell-cycle, when, for example, DNA is damaged, are ignored and damaged cells divide uncontrollably. The products of tumour suppressor genes function in all parts of the cell (e.g. cell surface, cytoplasm, nucleus) to prevent the passage of damaged cells through the cell-cycle (i.e. G1, S, G2, M and cytokinesis). A number of tumour suppressor genes have been isolated and sequenced. These include the Retinoblastoma gene (Rb), mutations in which are linked to cancers such as bone (osteocarcoma), bladder, small cell lung and breast cancer, as well as retinoblastoma. The Wilms Tumour 1 gene (WT-1), mutations that are linked to nephroblastoma and neurofibromatosis.

Arguably the tumour suppressor gene which has been the subject of the most intense research is p53. p53 encodes a protein which functions as a transcription factor and is a key regulator of the cell division cycle. It was discovered in 1978 (Lane and Crawford, 1979) as a protein shown to bind with affinity to the SV40 large T antigen. The p53 gene encodes a 393 amino acid polypeptide with a molecular weight of 53 kDa. One of the most important tumour suppression functions of p53 is its ability to induce apoptosis Apoptosis, or programmed cell death, is a process by which multi-cellular organisms regulate cell number and differentiation. The process is regulated by factors which either induce or prevent apoptosis. Inducers of apoptosis include Bcl-2 family members, caspase family members and their associated factors Apaf-1 and Fadd. Caspases are synthesised as proenzymes which become activated after proteolytic cleavage. The active caspase then induces many of the morphological and biochemical changes associated with apoptosis. Mitochondria play a pivotal role in the activation process through the release of pro-apoptotic factors such as cytochrome c, AIF and Diablo. The release from mitochondria is controlled by the Bcl-2 family of proteins; (e.g. Bcl-2 and Bcl-x1 inhibit release; Bax and Bak induce release).

The polypeptide referred to as iASPP that is described in WO02/12325 is a further example of an agent involved in the regulation of apoptosis.

SUMMARY

We describe a variant iASPP polypeptide which has characteristics which are distinct from those described in W02/12325. The polypeptide, referred to as iASPP6C, is extended at its amino terminus and binds preferentially to p53 when compared to iASPP. iASPP C6 preferentially binds p53 when compared to the shorter version described in W02/12325. The shorter version preferentially binds the apoptosis inducer protein Bcl 2.

iASPP C6 is a ubiquitinated polypeptide which likely controls the turnover of iASPP C6 in vivo. Ubiquitin is a small protein made up of 76 amino acids which is highly conserved across species. The most important function assigned to ubiquitin is in regulating protein turnover. Research in recent years has identified many accessory proteins involved in ubiquitin induced proteolysis. The first step is the ligation of ubiquitin to a target protein which is destined for degradation. This is mediated by three proteins referred to as E1, E2 and E3. Ubiquitin is first activated by E1 activating enzyme, a homodimer composed of two identical 105 kDa subunits which is ligated to ubiquitin via a thioester bond. Following activation the E1: ubiquitin conjugate is transported by E2 (referred to as a carrier protein). The E2 proteins vary markedly in size but do have some conserved elements. The E2 protein accepts the ubiquitin from E1 and forms a second complex again via a thioester bond. The E3 protein may or may not become involved in the final step, which is the transfer of ubiquitin to a protein substrate. This is followed by recognition by a protease, which degrades the ubiquitinated protein. The protease may be part of a structure referred to as the proteosome which is a large multi-subunit complex of proteases and associated co-factors. In some examples proteins can become polyubiqitinated, which results from ubiquitin proteins being ligated to ubiquitin proteins, which are already ligated to a target protein.

According to an aspect of the invention there is provided an isolated polypeptide wherein said polypeptide is represented by the amino acid sequence as shown in FIG. 1a, or a variant polypeptide which variant is modified by addition, deletion or substitution of at least one amino acid residue characterised in that said polypeptide has the following characteristics:

i) a polypeptide which preferentially binds the tumour suppressor polypeptide p53 to inhibit the pro-apoptotic activity of p53 when compared to a polypeptide, or variant thereof, as represented by the amino acid sequence as shown in FIG. 2a;

ii) a polypeptide which includes at least one amino acid residue which residue is ubiquitinated; and iii) a polypeptide which comprises an amino-terminal polypeptide domain wherein said domain is represented between amino acid 1 and 483 of the amino acid sequence shown in FIG. 1a.

In a preferred embodiment of the invention said polypeptide preferentially binds p53 when compared to a polypeptide represented by the amino acid sequence shown in FIG. 2a.

In a further preferred embodiment of the invention said polypeptide is modified by addition, deletion or substitution of at least one amino acid residue wherein said modification is between amino acid residues +1 and +483 of the amino acid sequence presented in FIG. 1a.

Assays to determine the binding of polypeptides, which are herein disclosed, to for example, p53 are known in the art and described in the present application.

In a further preferred embodiment of the invention said polypeptide comprises the amino acid sequence shown in FIG. 1a. Preferably said polypeptide consists of the amino acid sequence shown in FIG. 1a.

According to an aspect of the invention there is provided an isolated nucleic acid molecule wherein said nucleic acid molecule encodes a polypeptide according to the invention.

In a preferred embodiment of the invention said nucleic acid molecule is represented by the nucleic acid sequence shown in FIG. 1b or a nucleic acid molecule which hybridises to the sequence shown in FIG. 1b under stringent hybridisation conditions and which encodes a polypeptide according to the invention.

In a preferred embodiment of the invention said nucleic acid molecule consists of the nucleic acid sequence shown in FIG. 1b.

In a further preferred embodiment of the invention said isolated nucleic acid molecule is a cDNA. In an alternative preferred embodiment of the invention said nucleic acid molecule is genomic DNA.

According to a further aspect of the invention there is provided a vector comprising a nucleic acid molecule according to the invention. Preferably said vector is an expression vector adapted for recombinant expression of said polypeptide.

Preferably, said vector is adapted for prokaryotic gene expression. In an alternative embodiment of the invention said vector is adapted for eukaryotic gene expression.

Typically said adaptation includes, by example and not by way of limitation, the provision of transcription control sequences (promoter sequences) which mediate cell/tissue specific expression. These promoter sequences may be cell/tissue specific, inducible or constitutive.

Promoter is an art recognised term and includes the following features which are provided by example only, and not by way of limitation. Enhancer elements are cis acting nucleic acid sequences often found 5' to the transcription initiation site of a gene (enhancers can also be found 3' to a gene sequence or even located in intronic sequences and is therefore position independent). Enhancers function to increase the rate of transcription of the gene to which the enhancer is linked. Enhancer activity is responsive to traits acting transcription factors (polypeptides) which have been shown to bind specifically to enhancer elements. The binding/activity of transcription factors (please see Eukaryotic Transcription Factors, by David S Latchman, Academic Press Ltd, San Diego) is responsive to a number of environmental cues which include, by example and not by way of limitation, intermediary metabolites or environmental effectors, for example temperature.

Promoter elements also include so-called TATA box and RNA polymerase initiation selection (RIS) sequences which function to select a site of transcription initiation. These sequences also bind polypeptides which function, inter alia, to facilitate transcription initiation selection by RNA polymerase.

Adaptations also include the provision of selectable markers and autonomous replication sequences which both facilitate the maintenance of said vector in either the eukaryotic cell or prokaryotic host. Vectors which are maintained autonomously are referred to as episomal vectors. Episomal vectors are desirable since these molecules can incorporate large DNA fragments (30-50 kb DNA). Episomal vectors of this type are described in WO98/07876.

Adaptations which facilitate the expression of vector encoded genes include the provision of transcription termination/polyadenylation sequences. This also includes the provision of internal ribosome entry sites (IRES) which function to maximise expression of vector encoded genes arranged in bicistronic or multi-cistronic expression cassettes.

These adaptations are well known in the art. There is a significant amount of published literature with respect to expression vector construction and recombinant DNA techniques in general. Please see, Sambrook et al (1989) Molecular Cloning: A Laboratory Manual, Cold Spring Harbour Laboratory, Cold Spring Harbour, N.Y. and references therein; Marston, F (1987) DNA Cloning Techniques: A Practical Approach Vol III IRL Press, Oxford UK; DNA Cloning: F M Ausubel et al, Current Protocols in Molecular Biology, John Wiley & Sons, Inc. (1994).

According to a fourth aspect of the invention there is provided a method for the production of the polypeptide according to the invention comprising:

i) providing a cell transformed/transfected with a nucleic acid molecule according to the invention;

ii) growing said cell in conditions conducive to the manufacture of said polypeptide; and i) purifying said polypeptide from said cell or its growth environment.

In a preferred embodiment of the invention said nucleic acid molecule is the vector according to the invention.

In a preferred method of the invention said vector encodes, and thus said recombinant polypeptide is provided with, a secretion signal to facilitate purification of said polypeptide.

According to a further aspect of the invention there is provided an antibody which binds the polypeptide according to the invention characterised in that said antibody binds said polypeptide between amino acid residues +1 to +483 of the amino acid sequence shown in FIG. 1a.

Preferably said antibody does not bind said polypeptide represented by the sequence +484 to +828 of the amino acid sequence shown in FIG. 1a.

Antibodies, also known as immunoglobulins, are protein molecules which usually have specificity for foreign molecules (antigens). Immunoglobulins (Ig) are a class of structurally related proteins consisting of two pairs of polypeptide chains, one pair of light (L) (low molecular weight) chain (κ or λ), and one pair of heavy (H) chains (γ, α, μ, δ and ε), all four linked together by disulphide bonds. Both H and L chains have regions that contribute to the binding of antigen and that are highly variable from one Ig molecule to another. In addition, H and L chains contain regions that are non-variable or constant.

The L chains consist of two domains. The carboxy-terminal domain is essentially identical among L chains of a given type and is referred to as the "constant" (C) region. The amino terminal domain varies from L chain to L chain and contributes to the binding site of the antibody. Because of its variability, it is referred to as the "variable" (V) region.

The H chains of Ig molecules are of several classes, α, μ, σ, α, and γ (of which there are several sub-classes). An assembled Ig molecule consisting of one or more units of two identical H and L chains, derives its name from the H chain that it possesses. Thus, there are five Ig isotypes: IgA, IgM, IgD, IgE and IgG (with four sub-classes based on the differences in the 'constant' regions of the H chains, i.e., IgG1, IgG2, IgG3 and IgG4). Further detail regarding antibody structure and their various functions can be found in, Using Antibodies: A laboratory manual, Cold Spring Harbour Laboratory Press.

In a preferred embodiment of the invention said fragment is a Fab fragment.

In a further preferred embodiment of the invention said antibody is selected from the group consisting of: F(ab')$_2$, Fab, Fv and Fd fragments; and antibodies comprising CDR3 regions.

Preferably said fragments are single chain antibody variable regions (scFV's) or domain antibodies. If a hybridoma exists for a specific monoclonal antibody it is well within the knowledge of the skilled person to isolate scFv's from mRNA extracted from said hybridoma via RT PCR. Alternatively, phage display screening can be undertaken to identify clones expressing scFv's. Domain antibodies are the smallest binding part of an antibody (approximately 13 kDa). Examples of this technology is disclosed in U.S. Pat. No. 6,248,516, U.S. Pat. No. 6,291,158, U.S. Pat. No. 6,127,197 and EP0368684 which are all incorporated by reference in their entirety.

A modified antibody, or variant antibody and reference antibody, may differ in amino acid sequence by one or more substitutions, additions, deletions, truncations which may be present in any combination. Among preferred variants are those that vary from a reference polypeptide by conservative amino acid substitutions. Such substitutions are those that substitute a given amino acid by another amino acid of like characteristics. The following non-limiting list of amino acids are considered conservative replacements (similar): a) alanine, serine, and threonine; b) glutamic acid and asparatic acid; c) asparagine and glutamine d) arginine and lysine; e) isoleucine, leucine, methionine and valine and f) phenylalanine, tyrosine and tryptophan. Most highly preferred are variants which show enhanced biological activity.

Preferably said antibody is a humanised or chimeric antibody.

A chimeric antibody is produced by recombinant methods to contain the variable region of an antibody with an invariant or constant region of a human antibody.

A humanised antibody is produced by recombinant methods to combine the complementarity determining regions (CDRs) of an antibody with both the constant (C) regions and the framework regions from the variable (V) regions of a human antibody.

Chimeric antibodies are recombinant antibodies in which all of the V-regions of a mouse or rat antibody are combined with human antibody C-regions. Humanised antibodies are recombinant hybrid antibodies which fuse the complementarity determining regions from a rodent antibody V-region with the framework regions from the human antibody V-regions. The C-regions from the human antibody are also used. The complimentarily determining regions (CDRs) are the regions within the N-terminal domain of both the heavy and light chain of the antibody to where the majority of the variation of the V-region is restricted. These regions form loops at the surface of the antibody molecule. These loops provide the binding surface between the antibody and antigen.

Antibodies from non-human animals provoke an immune response to the foreign antibody and its removal from the circulation. Both chimeric and humanised antibodies have reduced antigenicity when injected to a human subject because there is a reduced amount of rodent (i.e. foreign) antibody within the recombinant hybrid antibody, while the human antibody regions do not elicit an immune response. This results in a weaker immune response and a decrease in the clearance of the antibody. This is clearly desirable when using therapeutic antibodies in the treatment of human diseases. Humanised antibodies are designed to have less "foreign" antibody regions and are therefore thought to be less immunogenic than chimeric antibodies.

According to a further aspect of the invention the invention there is provided a polypeptide according to the invention for use as a pharmaceutical.

According to a further aspect of the invention there is provided a nucleic acid according to the invention for use as a pharmaceutical.

In a preferred embodiment of the invention said pharmaceutical further comprises a diluent, carrier or excipient.

When administered, the therapeutic compositions of the present invention are administered in pharmaceutically acceptable preparations. Such preparations may routinely contain pharmaceutically acceptable concentrations of salt, buffering agents, preservatives, compatible carriers, supplementary immune potentiating agents such as adjuvants and cytokines and optionally other therapeutic agents, such as chemotherapeutic agents.

The therapeutics of the invention can be administered by any conventional route, including injection or by gradual infusion over time. The administration may, for example, be oral, intravenous, intraperitoneal, intramuscular, intracavity, subcutaneous, or transdermal. When antibodies are used therapeutically, a preferred route of administration is by pulmonary aerosol. Techniques for preparing aerosol delivery systems containing antibodies are well known to those of skill in the art. Generally, such systems should utilize components which will not significantly impair the biological properties of the antibodies, such as the paratope binding capacity (see, for example, Sciarra and Cutie, "Aerosols," in Remington's Pharmaceutical Sciences, 18th edition, 1990, pp 1694-1712; incorporated by reference). Those of skill in the art can readily determine the various parameters and conditions for producing antibody aerosols without resort to undue experimentation. When using antisense preparations of the invention, slow intravenous administration is preferred.

The compositions of the invention are administered in effective amounts. An "effective amount" is that amount of a composition that alone, or together with further doses, produces the desired response. In the case of treating a particular disease, such as cancer, the desired response is inhibiting the progression of the disease. This may involve only slowing the progression of the disease temporarily, although more preferably, it involves halting the progression of the disease permanently. This can be monitored by routine methods or can be monitored according to diagnostic methods of the invention discussed herein.

Such amounts will depend, of course, on the particular condition being treated, the severity of the condition, the individual patient parameters including age, physical condition, size and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however that a patient may insist upon a lower dose or tolerable dose for medical reasons, psychological reasons or for virtually any other reasons.

The pharmaceutical compositions used in the foregoing methods preferably are sterile and contain an effective amount of for example, a dominant negative iASPPC6 or nucleic acid encoding a dominant negative iASPPC6, for producing the desired response in a unit of weight or volume suitable for administration to a patient. The response can, for example, be measured by determining the signal transduction inhibited by the dominant negative iASPP C6, composition via a reporter system, by measuring downstream effects such as gene expression, or by measuring the physiological effects of the iASPPC6 composition, such as regression of a tumour, decrease of disease symptoms, modulation of apoptosis, etc.

The doses of dominant negative iASPPC6 polypeptide or nucleic acid administered to a subject can be chosen in accordance with different parameters, in particular in accordance with the mode of administration used and the state of the subject. Other factors include the desired period of treatment. In the event that a response in a subject is insufficient at the initial doses applied, higher doses (or effectively higher doses by a different, more localized delivery route) may be employed to the extent that patient tolerance permits.

In general, doses of dominant negative iASPPC6 are formulated and administered in doses between 1 ng and about 500 mg, and between 10 ng and 100 mg, according to any standard procedure in the art. Where nucleic acids encoding dominant negative iASPPC6 are employed, doses of between 1 ng and 0.1 mg generally will be formulated and administered according to standard procedures. Other protocols for the administration of iASPPC6 compositions will be known to one of ordinary skill in the art, in which the dose amount, schedule of injections, sites of injections, mode of administration (e.g., intra-tumoral) and the like vary from the foregoing. Administration of iASPPC6 compositions to mammals other than humans, e.g. for testing purposes or veterinary therapeutic purposes, is carried out under substantially the same conditions as described above. A subject, as used herein, is a mammal, preferably a human, and including a non-human primate, cow, horse, pig, sheep, goat, dog, cat or rodent.

When administered, the pharmaceutical preparations of the invention are applied in pharmaceutically-acceptable amounts and in pharmaceutically-acceptable compositions. The term "pharmaceutically acceptable" means a non-toxic material that does not interfere with the effectiveness of the biological activity of the active ingredients. Such preparations may routinely contain salts, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts.

iASPPC6 compositions may be combined, if desired, with a pharmaceutically-acceptable carrier. The term "pharmaceutically-acceptable carrier" as used herein means one or more compatible solid or liquid fillers, diluents or encapsulating substances which are suitable for administration into a human. The term "carrier" denotes an organic or inorganic ingredient, natural or synthetic, with which the active ingredient is combined to facilitate the application. The components of the pharmaceutical compositions also are capable of being co-mingled with the molecules of the present invention, and with each other, in a manner such that there is no interaction which would substantially impair the desired pharmaceutical efficacy.

The pharmaceutical compositions may contain suitable buffering agents, including: acetic acid in a salt; citric acid in a salt; boric acid in a salt; and phosphoric acid in a salt.

The pharmaceutical compositions also may contain, optionally, suitable preservatives, such as: benzalkonium chloride; chlorobutanol; parabens and thimerosal.

The pharmaceutical compositions may conveniently be presented in unit dosage form and may be prepared by any of the methods well-known in the art of pharmacy. All methods include the step of bringing the active agent into association with a carrier which constitutes one or more accessory ingredients. In general, the compositions are prepared by uniformly and intimately bringing the active compound into association with a liquid carrier, a finely divided solid carrier, or both, and then, if necessary, shaping the product.

Compositions suitable for oral administration may be presented as discrete units, such as capsules, tablets, lozenges, each containing a predetermined amount of the active compound. Other compositions include suspensions in aqueous liquids or non-aqueous liquids such as a syrup, elixir or an emulsion.

Compositions suitable for parenteral administration conveniently comprise a sterile aqueous or non-aqueous preparation of iASPP C6 polypeptides or nucleic acids, which is preferably isotonic with the blood of the recipient. This preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Carrier formulation suitable for oral, subcutaneous, intravenous, intramuscular, etc. administrations can be found in Remington's Pharmaceutical Sciences, Mack Publishing Co., Easton, Pa.

In a preferred embodiment of the invention said nucleic acid molecule is an inhibitory RNA (RNAi) molecule or antisense nucleic acid molecule.

In a preferred embodiment of the invention said nucleic acid molecule is selected from the group consisting of an antisense molecule or an inhibitory RNA molecule designed with reference to the nucleic acid sequence shown in FIG. 1b. Preferably said antisense or inhibitory RNA molecule is designed to that part of said nucleic acid sequence which encodes an amino acid sequence as defined by amino acid residues +1 to +483 as shown in FIG. 1a.

As used herein, the term "antisense molecule" or "antisense" describes an oligonucleotide that is an oligoribonucleotide, oligodeoxyribonucleotide, modified oligoribonucleotide, or modified oligodeoxyribonucleotide which hybridises under physiological conditions to DNA comprising a particular gene or to an mRNA transcript of that gene and, thereby, inhibits the transcription of that gene and/or the translation of that mRNA. The antisense molecules are designed so as to interfere with transcription or translation of a target gene upon hybridisation with the target gene or transcript. Those skilled in the art will recognise that the exact length of the antisense oligonucleotide and its degree of complementarity with its target will depend upon the specific target selected, including the sequence of the target and the particular bases which comprise that sequence. It is preferred that the antisense oligonucleotide be constructed and arranged so as to bind selectively with the target under physiological conditions, i.e., to hybridise substantially more to the target sequence than to any other sequence in the target cell under physiological conditions. Based upon the iASPP6C nucleic acid sequences provided herein, or upon allelic or homologous genomic and/or cDNA sequences, one of skill in the art can easily choose and synthesise any of a number of appropriate antisense molecules for use in accordance with the present invention. For example, a "gene walk" comprising a series of oligonucleotides of 15-30 nucleotides spanning the length of iASPP6C nucleic acid can be prepared, followed by testing for inhibition of the corresponding iASPP6C expression. Optionally, gaps of 5-10 nucleotides can be left between the oligonucleotides to reduce the number of oligonucleotides synthesised and tested.

In order to be sufficiently selective and potent for inhibition, such antisense oligonucleotides should comprise at least 10 and, more preferably, at least 15 consecutive bases which are complementary to the target, although in certain cases modified oligonucleotides as short as 7 bases in length have been used successfully as antisense oligonucleotides (Wagner et al., *Nature Biotechnol.* 14:840-844, 1996). Most preferably, the antisense oligonucleotides comprise a complementary sequence of 20-30 bases. Although oligonucleotides may be chosen which are antisense to any region of the gene or mRNA transcripts, in preferred embodiments the antisense oligonucleotides correspond to N-terminal or 5' upstream sites such as translation initiation, transcription initiation or promoter sites. In addition, 3'-untranslated regions may be targeted. Targeting to mRNA splicing sites has also been used in the art but may be less preferred if alternative mRNA splicing occurs. In addition, the antisense is targeted, preferably, to sites in which mRNA secondary structure is not expected (see, e.g., Sainio et al., *Cell Mol. Neurobiol.* 14(5): 439-457, 1994) and at which proteins are not expected to bind. Finally, although iASPP 6C cDNA sequences are disclosed herein, one of ordinary skill in the art may easily derive the genomic DNA corresponding to the cDNAs. Thus, the present invention also provides for antisense oligonucleotides which are complementary to iASPP6C genomic DNA. Similarly, antisense to allelic or homologous cDNAs and genomic DNAs are enabled without undue experimentation.

In one set of embodiments, the antisense oligonucleotides of the invention may be composed of "natural" deoxyribonucleotides, ribonucleotides, or any combination thereof. That is, the 5' end of one native nucleotide and the 3' end of another native nucleotide may be covalently linked, as in natural systems, via a phosphodiester internucleoside linkage. These oligonucleotides may be prepared by art recognised methods which may be carried out manually or by an automated synthesiser. They also may be produced recombinantly by vectors.

In a preferred embodiment of the invention there is provided a transcription cassette comprising a nucleic acid sequence operatively linked to a promoter which promoter transcribes said nucleic acid molecule to produce an antisense nucleic acid molecule, said sequence selected from the group consisting of:
 i) a nucleic acid sequence, or part thereof, as represented in FIG. 1*b*;
 ii) a nucleic acid sequence which hybridises to the sense sequence presented in FIG. 1*b* and which encodes a polypeptide according to the invention.

A recent technique to specifically ablate gene function is through the introduction of double stranded RNA, also referred to as inhibitory RNA (RNAi), into a cell which results in the destruction of mRNA complementary to the sequence included in the RNAi molecule. The RNAi molecule comprises two complementary strands of RNA (a sense strand and an antisense strand) annealed to each other to form a double stranded RNA molecule. The RNAi molecule is typically derived from exonic or coding sequence of the gene which is to be ablated.

Recent studies suggest that RNAi molecules ranging from 100-1000 bp derived from coding sequence are effective inhibitors of gene expression. Surprisingly, only a few molecules of RNAi are required to block gene expression which implies the mechanism is catalytic. The site of action appears to be nuclear as little if any RNAi is detectable in the cytoplasm of cells indicating that RNAi exerts its effect during mRNA synthesis or processing.

In a further preferred embodiment of the invention there is provided a transcription cassette comprising a nucleic acid molecule, or part thereof, selected from the group consisting of:
 i) a nucleic acid molecule represented by the nucleic acid sequence in FIG. 1*b*;
 ii) a nucleic acid molecule which hybridises to the sequence in (i) above and which encodes a polypeptide according to the invention; or
 iii) a nucleic acid molecule which is degenerate because of the genetic code to the sequences defined in (i) and (ii) above; wherein said cassette is adapted such that both sense and antisense nucleic acid molecules are transcribed from said cassette.

In a preferred embodiment of the invention said cassette is provided with at least two promoters adapted to transcribe both sense and antisense strands of said nucleic acid molecule.

In a further preferred embodiment of the invention said cassette comprises a nucleic acid molecule wherein said molecule comprises a first part linked to a second part wherein said first and second parts are complementary over at least part of their sequence and further wherein transcription of said nucleic acid molecule produces an RNA molecule which forms a double stranded region by complementary base pairing of said first and second parts.

In a preferred embodiment of the invention said first and second parts are linked by at least one nucleotide base.

In a preferred embodiment of the invention said first and second parts are linked by 2, 3, 4, 5, 6, 7, 8, 9 or at least 10 nucleotide bases.

In a further preferred embodiment of the invention the length of the RNAi molecule is between 100 bp-1000 bp. More preferably still the length of RNAi is selected from 100 bp; 200 bp; 300 bp; 400 bp; 500 bp; 600 bp; 700 bp; 800 bp; 900 bp; or 1000 bp. More preferably still said RNAi is at least 1000 bp.

In an alternative preferred embodiment of the invention the RNAi molecule is between 15 bp and 25 bp, preferably said molecule is 21 bp.

In a preferred embodiment of the invention said cassette is part of a vector.

According to a further aspect of the invention there is provided a screening method to identify an agent which modulates the interaction of p53 binding proteins with a p53 polypeptide wherein said method comprises the following steps of:
 i) forming a preparation comprising a polypeptide according to the invention and a p53 polypeptide, or sequence variant thereof, and at least on agent to be tested;
 ii) determining the activity of said agent with respect to the binding of said polypeptide to p53 polypeptide.

According to a further aspect of the invention there is provided a screening method for the identification of an agent which modulates the interaction of Bcl-2 binding polypeptides with a Bcl-2 polypeptide wherein said method comprises the steps of:

i) forming a preparation comprising a polypeptide as represented by the amino acid sequence shown in FIG. 2a, or a variant polypeptide which is modified by addition deletion or substitution of at least one amino acid residue and a Bcl-2 polypeptide or variant thereof, and at least one agent to be tested; and ii) determining the activity of said agent with respect to the binding of said polypeptide for said Bcl-2 polypeptide.

According to a yet further aspect of the invention there is provided a screening method to identify agents which modulate the ubiquitination of a polypeptide according to the invention comprising the steps of:

i) forming a preparation comprising a polypeptide according to the invention, a ubiquitin polypeptide or variant thereof, polypeptide(s) with the specific activity associated with ubiquitin conjugating polypeptides and at least one agent to be tested;

ii) determining the activity of said agent with respect to the conjugation of ubiquitin to said polypeptide.

In a preferred method of the invention said agent is a peptide or polypeptide.

In a preferred method of the invention said peptide is at least 6 amino acid residues in length. Preferably the length of said peptide/polypeptide is selected from the group consisting of: at least 7 amino acid residues; 8, 9, 10, 11, 12, 13, 14, 15, 16, 17, 18, 19, or 20 amino acid residues in length. Alternatively the length of said peptide/polypeptide is at least 20 amino acid residues; 30; 40; 50; 60; 70; 80; 90; or 100 amino acid residues in length.

It will be apparent to one skilled in the art that modification to the amino acid sequence of peptides agents could enhance the binding and/or stability of the peptide with respect to its target sequence. In addition, modification of the peptide may also increase the in vivo stability of the peptide thereby reducing the effective amount of peptide necessary to inhibit p53 binding of iASPP. This would advantageously reduce undesirable side effects which may result in vivo. Modifications include, by example and not by way of limitation, acetylation and amidation. Alternatively or preferably, said modification includes the use of modified amino acids in the production of recombinant or synthetic forms of peptides. It will be apparent to one skilled in the art that modified amino acids include, by way of example and not by way of limitation, 4-hydroxyproline, 5-hydroxylysine, $N^6$-acetyllysine, $N^6$-methyllysine, $N^6,N^6$-dimethyllysine, $N^6,N^6,N^6$-trimethyllysine, cyclohexyalanine, D-amino acids, ornithine. Other modifications include amino acids with a $C_2$, $C_3$ or $C_4$ alkyl R group optionally substituted by 1, 2 or 3 substituents selected from halo (eg F, Br, I), hydroxy or $C_1$-$C_4$ alkoxy. Modifications also include, by example and not by way of limitation, acetylation and amidation.

In a preferred embodiment of the invention said peptide sequence is acetylated. Preferably said acetylation is to the amino terminus of said peptide.

In a further preferred embodiment of the invention said peptide sequence is amidated. Preferably said amidation is to the carboxyl-terminus of said peptide.

It will also be apparent to one skilled in the art that peptides could be modified by cyclisation. Cyclisation is known in the art, (see Scott et al Chem Biol (2001), 8:801-815; Gellerman et al J. Peptide Res (2001), 57: 277-291; Dutta et al J. Peptide Res (2000), 8: 398-412; Ngoka and Gross J Amer Soc Mass Spec (1999), 10:360-363.

In a further preferred method of the invention said antagonist is an antibody or antibody binding part. Preferably said antibody is a monoclonal antibody or binding part thereof.

In an alternative preferred method of the invention said agent is an aptamer.

Nucleic acids have both linear sequence structure and a three dimensional structure which in part is determined by the linear sequence and also the environment in which these molecules are located. Conventional therapeutic molecules are small molecules, for example, peptides, polypeptides, or antibodies that bind target molecules to produce an agonistic or antagonistic effect. It has become apparent that nucleic acid molecules also have potential with respect to providing agents with the requisite binding properties which may have therapeutic utility. These nucleic acid molecules are typically referred to as aptamers. Aptamers are small, usually stabilised, nucleic acid molecules which comprise a binding domain for a target molecule. A screening method to identify aptamers is described in U.S. Pat. No. 5,270,163 which is incorporated by reference. Aptamers are typically oligonucleotides which may be single stranded oligodeoxynucleotides, oligoribonucleotides, or modified oligodeoxynucleotide or oligoribonucleotides.

The term "modified" encompasses nucleotides with a covalently modified base and/or sugar. For example, modified nucleotides include nucleotides having sugars which are covalently attached to low molecular weight organic groups other than a hydroxyl group at the 3' position and other than a phosphate group at the 5' position. Thus modified nucleotides may also include 2' substituted sugars such as 2'-O-methyl-; 2-O-alkyl; 2-O-allyl; 2'-S-alkyl; 2'-S-allyl; 2'-fluoro-; 2'-halo or 2; azido-ribose, carbocyclic sugar analogues a-anomeric sugars; epimeric sugars such as arabinose, xyloses or lyxoses, pyranose sugars, furanose sugars, and sedoheptulose.

Modified nucleotides are known in the art and include by example and not by way of limitation; alkylated purines and/or pyrimidines; acylated purines and/or pyrimidines; or other heterocycles. These classes of pyrimidines and purines are known in the art and include, pseudoisocytosine; N4, N4-ethanocytosine; 8-hydroxy-N6-methyladenine; 4-acetylcytosine, 5-(carboxyhydroxylmethyl) uracil; 5-fluorouracil; 5-bromouracil; 5-carboxymethylaminomethyl-2-thiouracil; 5-carboxymethylaminomethyl uracil; dihydrouracil; inosine; N6-isopentyl-adenine; 1-methyladenine; 1-methylpseudouracil; 1-methylguanine; 2,2-dimethylguanine; 2-methyladenine; 2-methylguanine; 3-methylcytosine; 5-methylcytosine; N6-methyladenine; 7-methylguanine; 5-methylaminomethyl uracil; 5-methoxy amino methyl-2-thiouracil; β-D-mannosylqueosine; 5-methoxycarbonylmethyluracil; 5-methoxyuracil; 2 methylthio-N6-isopentenyladenine; uracil-5-oxyacetic acid methyl ester; psueouracil; 2-thiocytosine; 5-methyl-2 thiouracil, 2-thiouracil; 4-thiouracil; 5-methyluracil; N-uracil-5-oxyacetic acid methylester; uracil 5-oxyacetic acid; queosine; 2-thiocytosine; 5-propyluracil; 5-propylcytosine; 5-ethyluracil; 5-ethylcytosine; 5-butyluracil; 5-pentyluracil; 5-pentylcytosine; and 2,6,-diaminopurine; methylpsuedouracil; 1-methylguanine; 1-methylcytosine.

The aptamers of the invention are synthesized using conventional phosphodiester linked nucleotides and synthesized using standard solid or solution phase synthesis techniques which are known in the art. Linkages between nucleotides may use alternative linking molecules. For example, linking groups of the formula P(O)S, (thioate); P(S)S, (dithioate);

P(O)NR'2; P(O)R'; P(O)OR6; CO; or CONR'2 wherein R is H (or a salt) or alkyl (1-12C) and R6 is alkyl (1-9C) is joined to adjacent nucleotides through —O— or —S—. The binding of aptamers to a target polypeptide is readily tested by assays hereindisclosed.

An embodiment of the invention will now be described by example only and with reference to the following figures:

BRIEF DESCRIPTION OF THE DRAWINGS

FIG. 1a is the amino acid sequence of iASPP C6 protein (SEQ ID NO: 1), amino acid sequence underlined is identical to iASPP; FIG. 1b is the nucleic acid sequence of iASPP6C (SEQ ID NO: 2);

FIG. 2a is the amino acid sequence of iASPP (SEQ ID NO: 3); FIG. 2b is the nucleic acid sequence of iASPP (SEQ ID NO: 4);

FIG. 3 is a sequence alignment of full length iASPP6C (SEQ ID NO: 1 and 2) and iASPP (SEQ ID NO: 3 and 4);

FIG. 4A illustrates the expression of iASPP expression in various cell lines. Full length iASPP 6C is detected at about 100 kDa. The samples probed with antibody LX049.3 are: 2.1 kb iASPP in vitro translated; RKO (colon cancer cell line); HeLa; 293 (kidney); MCF7 (breast); SaOS2 (osteosarcoma); HBL100 (breast); H1299 (lung); U937 (lung); U2OS (osteosarcoma)

FIG. 7 illustrates that p53 preferentially binds to full length iASPP6C, while Bcl-2 preferentially binds iASPP;

Figure 4B:
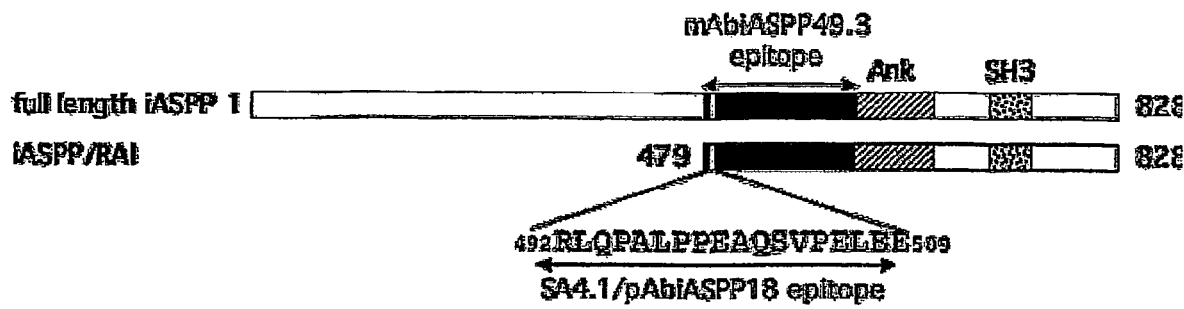
FIGS. 4B, 4C and 4D illustrates that iASPP6C can be detected by distinct antibodies raised against sequences within both iASPP and iASPP6C. 4B is a diagram illustrating the relative positions of the antigens used to generate antibodies LX049.3, SA4.1 and pAb18; 4C shows that both iASPP6C and iASPP cDNAs were translated in vitro using unlabelled amino acids. A control reaction was run alongside which contained empty vector. The band observed between the two iASPP proteins in the blot probed with LX049.3 is non-specific. 4D shows the expression levels of iASPP6C and iASPP were detected in cell lines using LX049.3. In vitro translated products of the iASPP and iASPP6C cDNAs (IVT) are loaded as positive controls. The positions of the molecular weight markers are shown on the right. Anti PCNA antibody PC-10 was used as a loading control for the cell lysates.
Figure 4C:
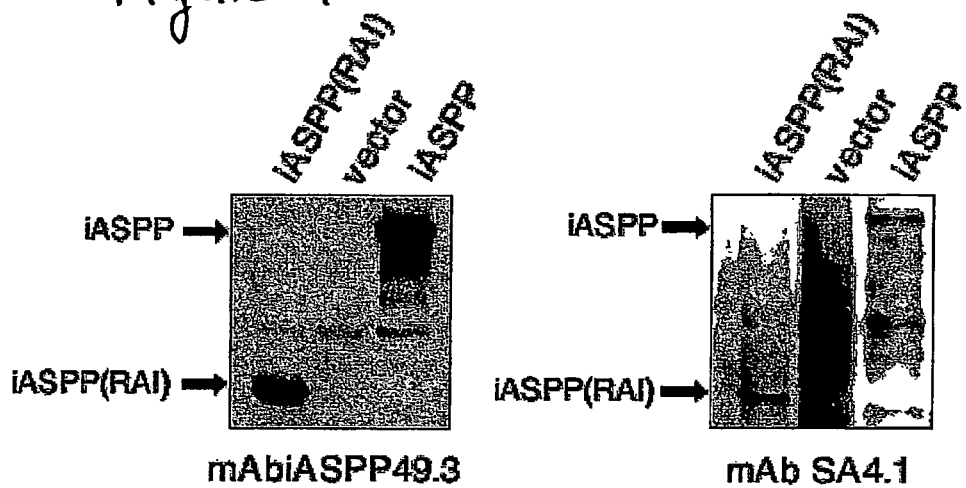
Figure 4D:
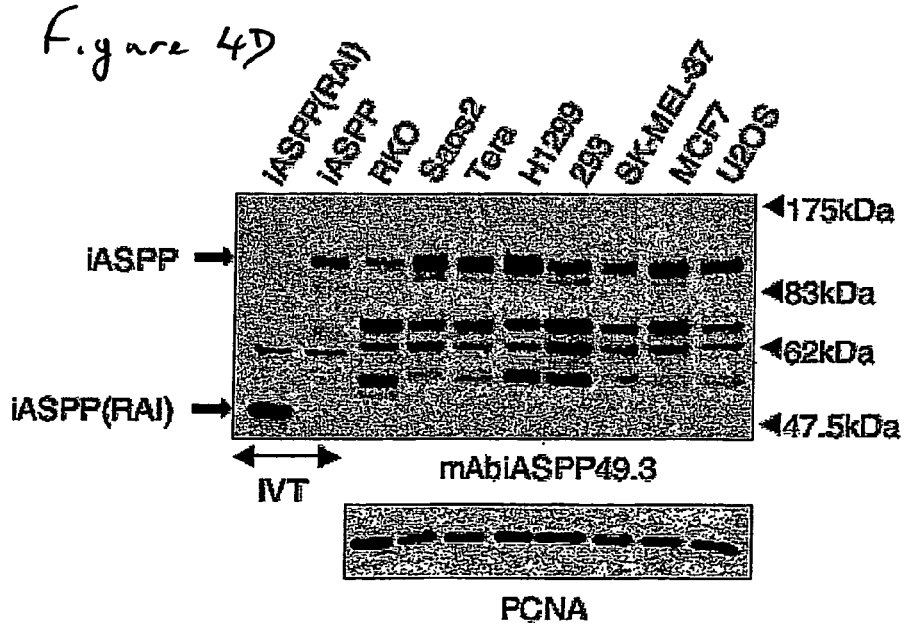
Figure 5:
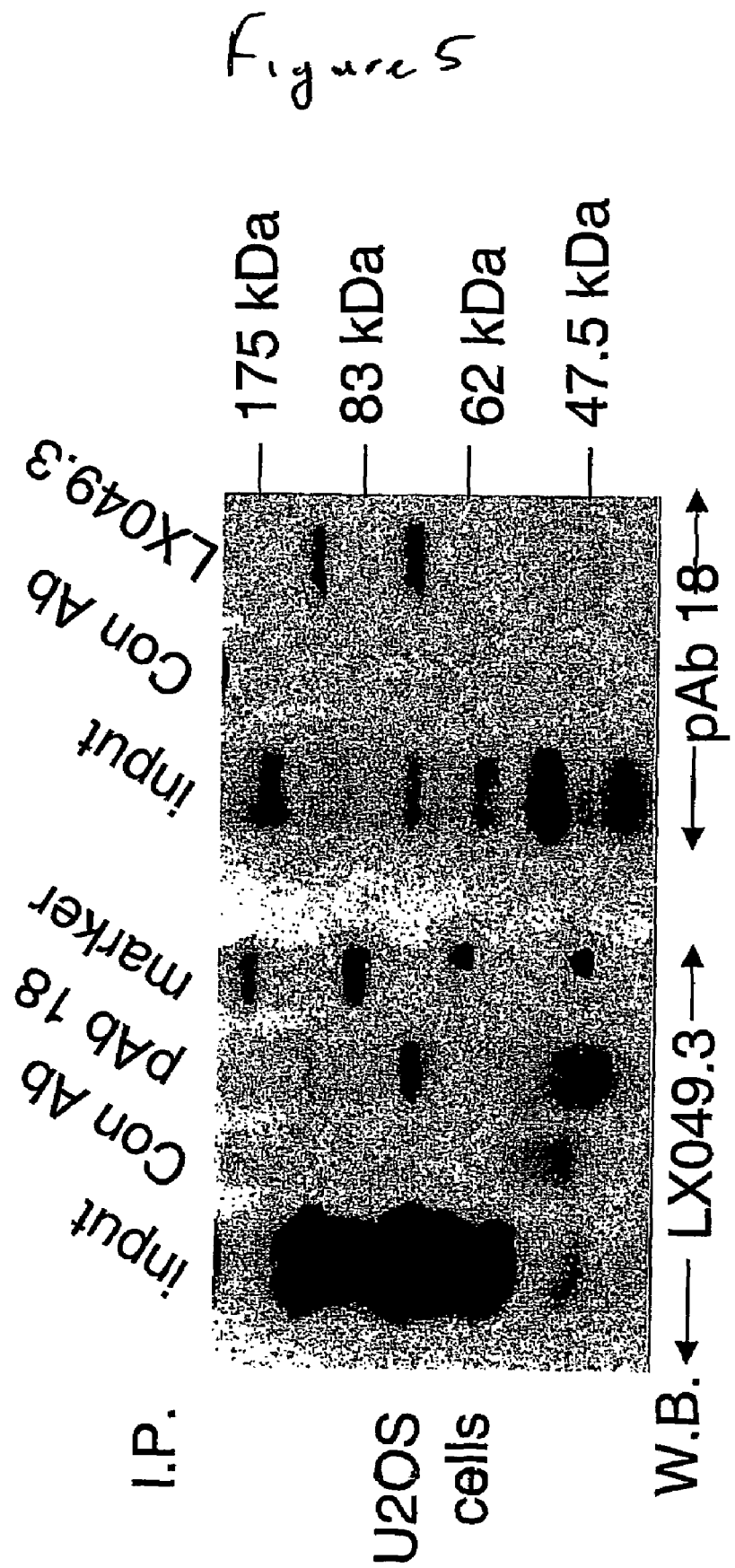
FIG. 5 illustrates an immunoprecipitation/western blot using two different iASPP antibodies: LX049.3 is a mouse monoclonal while pAb18 is a rabbit antibody (epitopes are given in the peptide alignment, see FIG. 3)
Figure 6A:
FIGS. 6a and 6b illustrates that iASPP 6C is ubiquitinated. This process results in the generation of the 83 kDa fragment, which is abolished in the presence of MG132 (ubiquitin-proteosome inhibitor). Ubiquitination also appears to be dependent on cell density. The cells were split according the cell density required and MG132 was added the next day (16-24 hrs later)
Figure 6B:
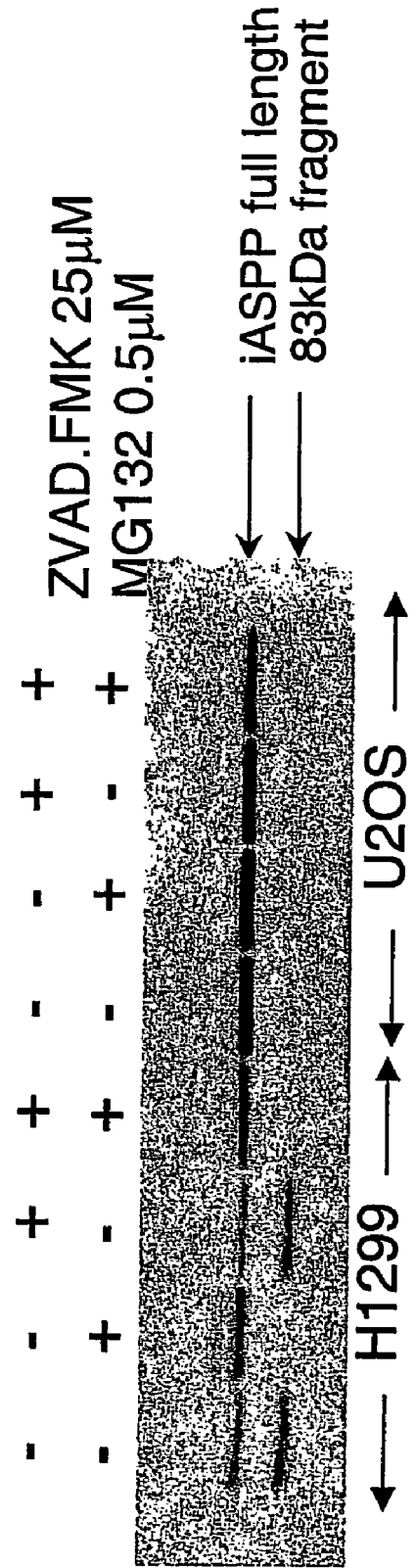
Figure 8:
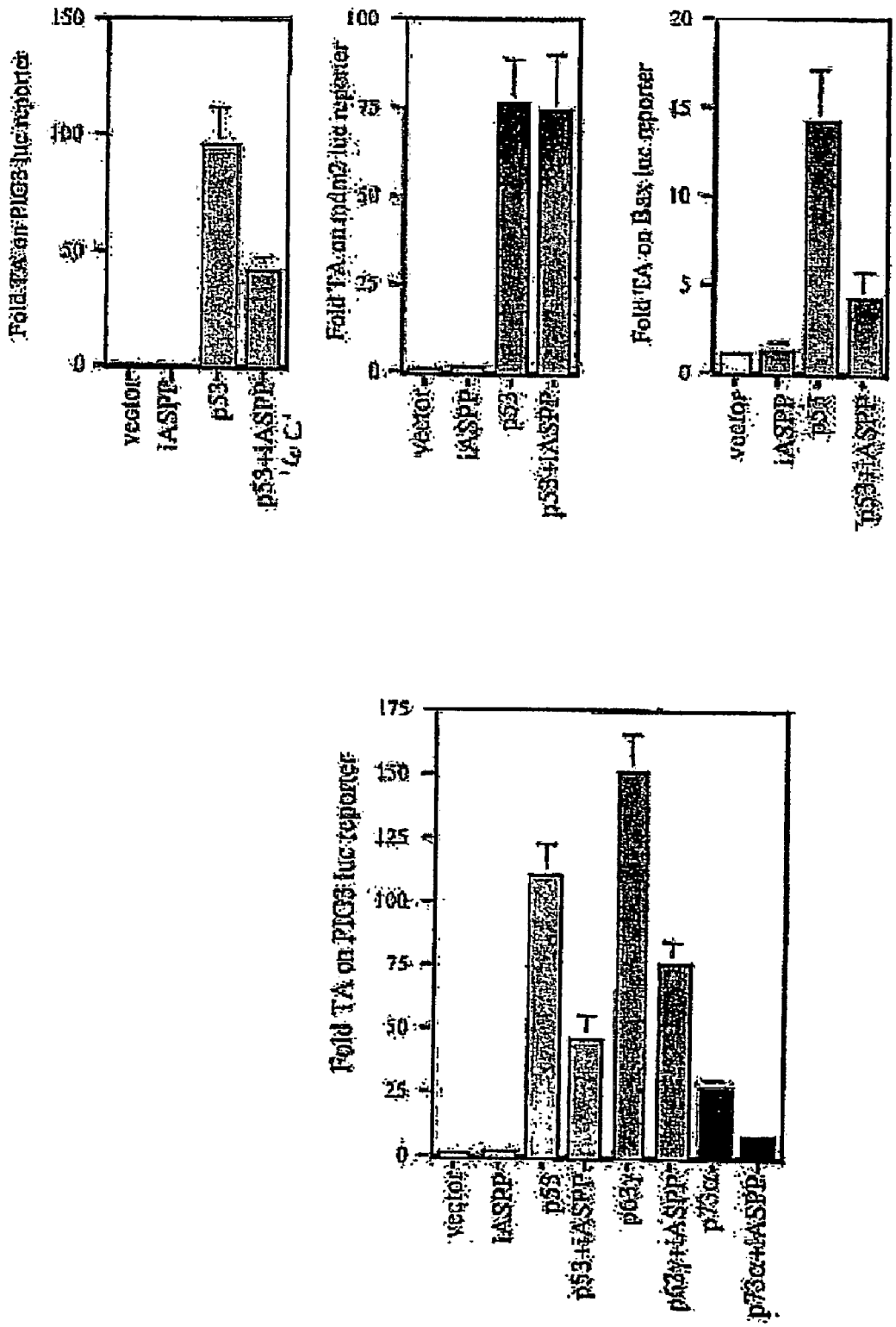
FIG. 8 illustrates the activity of the full length iASPP6C in cells and that iASPP and p53 are involved in the activation of apoptotic genes but not cell cycle regulatory genes, and that it also interacts with p63 and p73.
Figure 9:
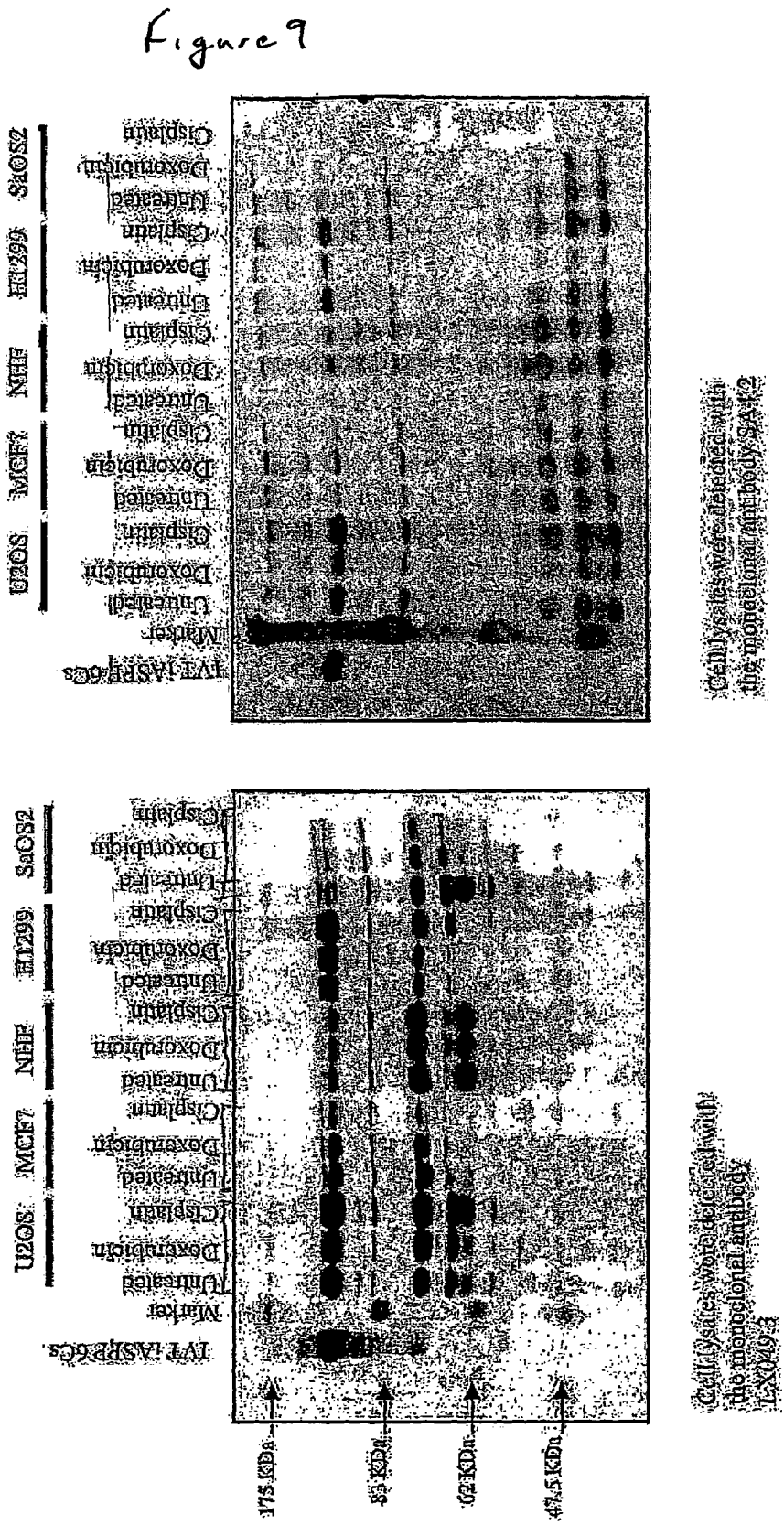
FIG. 9 illustrates that the full length iASPP6C is preferentially expressed in cells rather than iASPP but at different expression levels.

The N-terminus of iASPP6C causes its localisation to the cytoplasm: (a) LX049.3 was used to detect iASPP6C in Saos-2 and H1299 cells. Either transfected or endogenous iASPP6C was analysed in Saos-2 cells, alongside endogenous iASPP6C in H1299 cells. (b) V5 epitope-tagged constructs encoding the regions of iASPP were transfected into Saos-2 cells and their subcellular localisation determined by immunofluorescence using anti-V5 antibody.

The C-terminus of iASPP6C is required for the inhibition of p53. (a) Saos-2 cells were transfected with p53 and the indicated iASPP truncations, and apoptosis was detected by FACS. (b) Saos-2 cells were transfected with 1 µg of a luciferase reporter plasmid containing the PIG-3 promoter alongside 50 ng of p53 and 0.25 µg of the iASPP6C plasmids.

DETAILED DESCRIPTION

Materials and Methods

Cell Culture and Reagents

Cells were grown in culture in Dulbecco's modified Eagle medium (Invitrogen) supplemented with 10% foetal calf serum. The cells used in this study were Tera (testicular tumour cell line), RKO (colon carcinoma), Saos-2 (osteosarcoma), H1299 (lung carcinoma), 293 (embryonic kidney), SK-MEL-37 (melanoma), MCF7 (mammary epithelial) and U2OS (osteosarcoma). Anti-V5 antibody was purchased from Invitrogen. N-20 CD20Leu FITC-conjugated monoclonal antibody was from Becton Dickinson. Transfections throughout were performed by calcium phosphate precipitation.

Plasmids

The EST containing the cDNA encoding iASPP6C (I.M.A.G.E. clone 4994121) was obtained from MRC Geneservice (Cambridge, U.K.). The cDNA was subcloned into pcDNA3.1/V5-His-TOPO (Invitrogen). pcDNA3.1 iASPP, pcDNA3.1 ASPP2, pcDNA3.1 Ce-iASPP and pcDNA3 p53 have been described previously (Bergamaschi et al., 2003; Samuels-Lev et al., 2001). The iASPP6C truncations used in FIG. 10 were generated by PCR-directed cloning into pcDNA3.11V5-His-TOPO. A modified pcDNA3 vector that has had two V5 sequences inserted 5' of the polylinker was used to generate N-terminally V5-tagged iASPP6C.

Generation of Anti-iASPP Antibodies

Anti-iASPP6C antibodies pAb18 (rabbit polyclonal) and SA4.1 (mouse monoclonal) were raised against the peptide RLQPALPPEAQSVPELEE (amino acids 492 to 509 of iASPP6C; SEQ ID NO: 7). Anti iASPP6C mouse monoclonal antibody LX049.3 was raised against a C-terminal His-tagged fusion protein containing amino acids 459 to 639 of iASPP6C. The corresponding cDNA was amplified by PCR and subcloned into pCRT7/CTTOPO (Invitrogen). The recombinant iASPP6C fragment was generated in BL21 Star E. coli (Invitrogen) by incubation with 1 mM IPTG for 4 h followed by purification under denaturing conditions.

Electrophoresis and Immunoblotting

Cells were washed twice in PBS, then scraped into 1 ml PBS and pelleted at 400 g. The cells were lysed by incubating for 30 minutes at room temperature in 8 M urea, 1 M thiourea, 0.5% CHAPS, 50 mM DTT and 24 mM spermine, followed by centrifugation at 20 000 g for 20 minutes at 16° C. 30 µg protein was used for analysis by SDS-PAGE and immunoblotting as described previously (Yap et al., 2000).

Immunoprecipitation

Cells were lysed by incubating on ice in NP40 lysis buffer (50 mM Tris pH8.0, 150 mM NaCl, 1 mM EDTA, 1% NP40 and protease inhibitors (complete protease inhibitor cocktail, Roche)) for 45 minutes followed by centrifugation for 20 minutes at 20 000 g at 4° C. Between 0.5 and 2 mg lysate was precleared by rotating for 1 h at 4° C. with protein G sepharose beads (Amersham Biosciences). Following removal of the beads, the lysate was transferred to a fresh tube and rotated overnight with blocked protein G sepharose beads at 4° C. and approximately 1 µg of either a specific antibody or non-specific mouse or rabbit IgG (Sigma) as controls. The beads were then washed three times in ice cold NP40 lysis buffer and the resulting complexes analysed by SDS-PAGE and immunoblot.

Construction and Transfection of iASPP6C siRNA

Oligonucleotides containing 19 bases of sequence present in both iASPP6C and iASPP cDNAs were ligated into the pSuper expression plasmid as described previously (Brummelkamp et al., 2002). The plasmids were verified by sequencing. The complete sequences of the oligonucleotides used to generate the siRNA are as follows with the cDNA sequences shown in upper case:

sense,

```
sense,
5'gatccccTGTCAACTCCCCCGACAGCttcaagagaGCTGTCGGGGGAG
TTGACAtttttggaaa 3' (SEQ ID NO:5);

antisense,
5'agcttttccaaaaaTGTCAACTCCCCCGACAGCtctcttgaaGCTGTC
GGGGGAGTTGACAggg 3' (SEQ ID NO:6).
```

For transfection, 1×10⁶ H1299 cells were plated into 10 cm dishes. Cells were transfected with 3 µg of pMACS H-2K$^K$ alongside either pSuper or pSuper-si-RNA iASPP (10 µg). 48 h after transfection, cells expressing the pMACS H-2K$^K$ plasmid were separated using the MACS system (Miltenyi Biotec) according to the manufacturer's instructions. This gave rise to two populations of cells: H-2K$^K$ expressing (transfected) cells and non-expressing (non-transfected cells). Both cell populations were lysed with RIPA buffer (150 mM NaCl, 1 mM EDTA, 5 mM Tris pH8, 0.5% deoxycholate, 1% NP40, 0.1% SDS) on ice for 30 minutes followed by centrifugation at 20 000 g for 30 minutes at 4° C.

In Vitro Translation and In Vitro Immunoprecipitation p53 and iASPP6C were translated in vitro with 35S-methionine using the TNT T7 Quick coupled Transcription/Translation System (Promega). The reticulocyte lysates containing each protein were combined as indicated and incubated together for 1 h at 30° C. LX049.3 antibody immobilised on protein G sepharose beads was added to the binding reactions and rotated at 4° C. for 16 h. The beads were then washed with PBS. The bound proteins were released in SDS sample buffer and analysed by 10% SDS-PAGE. Results were visualised by autoradiography.

Transactivation

The transcriptional assay was carried out as described previously (Samuels-Lev et al., 2001).

Flow Cytometry

Flow cytometry 1×10⁶ Saos-2 cells were plated in 10 cm dishes 24-48 h prior to transfection. All cells were transfected with 2 µg of pCMV CD20 as a transfection marker. The following plasmids were transfected as appropriate at the stated amounts: pcDNA3 p53 (1 µg), pcDNA3.1 Ce-iASPP (7.5 µg), pcDNA3.1 iASPP (7.5 µg), pcDNA3.1 iASPP6C(1 µg), pcDNA3.1 ASPP2 (10 µg). 2 µg iASPP6C truncations were used in FIG. 11. Empty pcDNA3 vector was used to equalise the total amount of DNA in all samples. 36 h after transfection, both attached and floating cells were harvested and analysed as described previously (Hsieh et al., 1997).

Immunofluorescence

Saos-2 cells were seeded on cover slips in 24 well plates at 50% density and transfected with 0.5-3 µg of plasmid encoding the iASPP6C truncations. 24 h after transfection the cells were fixed with 200 µl of 4% paraformaldehyde in PBS for 12 minutes then permeabilised with 0.1% Triton-X100 in PBS for 4 minutes. Expression of the iASPP6C constructs was detected using anti-V5 antibody (1:100 dilution in 0.2% fish skin gelatin) for 40 minutes followed by a TRITC or FITC-conjugated secondary antibody for 20 minutes.

REFERENCES

Bergamaschi, D., Samuels, Y., Jin, B., Duraisingham, S., Crook, T. & Lu, X. (2004). *Mol. Cell. Biol.*, 24, 1341-1350.

Bergamaschi, D., Samuels, Y., O'Neil, N. J., Trigiante, G., Crook, T., Hsieh, J.-K., O'Connor, D. J., Zhong, S., Campargue, I., Tonilinson, M. L., Kuwabara, P. E. & Lu, X. (2003). *Nat. Genetics*, 33, 162-167.

Brummelkamp, T. R., Bernards, R. & Agami, R. (2002). *Science*, 296, 550-3.

Derry, W. B., Putzke, A. P. & Rothman, J. H. (2001). *Science*, 294, 591-595. Gorina, S. & Pavletich, N. P. (1996). *Science*, 274, 1001-1005.

Hsieh, J.-K, Fredersdorf, S., Kouzarides, T., Martin, K & Lu, X. (1997). *Genes Dev.*, 11, 1840-1852.

Iwabuchi, K., Bartel, P. L., Li, B., Marraccino, P & Fields, S. (1994). *Proc. Natl. Acad. Sci. USA*, 91, 6098-102.

Mihara, M., Erster, S., Zaika, A, Petrenko, O., Chittenden, T., Pancoska, P. & Moll, U. M. (2003). *Mol Cell*, 11, 577-90.

Naumovski, L. & Cleary, M. L. (1996). *Mol. Cell. Biol.*, 16, 3884-3892.

Sachdev, S., Hoffmann, A. & Hannink, M. (1998). *Mol. Cell. Biol.*, 18, 2524-2534.

Samuels-Lev, Y., O'Connor, D. J., Bergamaschi, D., Trigiante, G., Hsieh, J. K., Zhong, S., Campargue, I., Naumovski, L., Crook, T. & Lu, X. (2001). *Mol. Cell*, 8, 781-794.

Schumacher, B., Hofmann, K., Boulton, S. & Gartner, A. (2001). *Curr. Biol.*, 11, 1722-1727.

Slee, E. A., O'Connor, D. J. & Lu, X. (2004). *Oncogene*, 23, 2809-2818.

Vogelstein, B., Lane, D. & Levine, A. J. (2000). *Nature*, 408, 307-10.

Vousden, K. H. & Lu, X. (2002). *Nat. Rev. Cancer.*, 2, 594-604.

Yang, J.-P., Hori, M., Sanda, T. & Okamoto, T. (1999). *J. Biol. Chem.*, 274, 15662-15670.

Yap, D. B., Hsieh, J. K. & Lu, X. (2000). *J. Biol. Chem.*, 275, 37296-37302.

The invention claimed is:

1. An isolated polypeptide comprising the amino acid sequence as shown in SEQ ID NO: 1.

2. The polypeptide according to claim 1 wherein said amino acid sequence of said polypeptide consists of the amino acid sequence shown in SEQ ID NO: 1.

3. A composition comprising the polypeptide of claim 1 and a pharmaceutically-acceptable carrier.

4. An isolated polypeptide comprising amino acids 1-483 of SEQ ID NO: 1.

5. A composition comprising the isolated polypeptide of claim 4 and a pharmaceutically-acceptable carrier.

* * * * *

UNITED STATES PATENT AND TRADEMARK OFFICE
CERTIFICATE OF CORRECTION

PATENT NO. : 7,645,859 B2  Page 1 of 1
APPLICATION NO. : 10/582316
DATED : January 12, 2010
INVENTOR(S) : Lu et al.

It is certified that error appears in the above-identified patent and that said Letters Patent is hereby corrected as shown below:

On the cover page,

Item [*] Notice: Subject to any disclaimer, the term of this patent is extended or adjusted under 35 U.S.C. 154(b) by 70 days Delete the phrase "by 70 days" and insert -- by 225 days --

Signed and Sealed this

Fifteenth Day of June, 2010

David J. Kappos
*Director of the United States Patent and Trademark Office*